(12) United States Patent
Nordness et al.

(10) Patent No.: US 6,996,851 B2
(45) Date of Patent: Feb. 14, 2006

(54) PERMEABLE, CLOSE TO THE BODY LINER FOR SWIMWEAR

(75) Inventors: Cynthia H. Nordness, Oshkosh, WI (US); Kent A. Franklin, Appleton, WI (US); Katherine C. Wheeler, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 42 days.

(21) Appl. No.: 10/021,901

(22) Filed: Dec. 13, 2001

(65) Prior Publication Data

US 2003/0139720 A1 Jul. 24, 2003

(51) Int. Cl.
A41B 9/00 (2006.01)

(52) U.S. Cl. .......................... 2/78.3; 2/67; 2/69; 2/76; 2/80; 2/82; 2/272; 2/919

(58) Field of Classification Search .............. 2/67, 2/69, 76, 78.3, 80, 82, 272, 919
See application file for complete search history.

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 4,340,563 A | 7/1982 | Appel et al. |
| 4,663,220 A | 5/1987 | Wisneski et al. |
| 4,674,135 A | 6/1987 | Greene |
| 4,795,455 A | 1/1989 | Luceri et al. |
| RE33,106 E | 11/1989 | Beckestrom |
| 4,892,536 A | 1/1990 | DesMarais et al. |
| 4,940,464 A | 7/1990 | Van Gompel et al. |
| 4,990,147 A | 2/1991 | Freeland |
| 5,031,248 A | 7/1991 | Kemper |
| 5,046,272 A | 9/1991 | Vogt et al. |
| 5,104,116 A | 4/1992 | Pohjola |
| 5,224,405 A | 7/1993 | Pohjola |
| 5,226,992 A | 7/1993 | Morman |
| 5,269,755 A | 12/1993 | Bodicky |
| 5,366,786 A * | 11/1994 | Connor et al. .............. 428/171 |
| 5,388,275 A | 2/1995 | Oram |
| 5,509,913 A | 4/1996 | Yeo |
| D377,980 S | 2/1997 | Slingland |

(Continued)

FOREIGN PATENT DOCUMENTS

EP 0 217 032 4/1987

(Continued)

Primary Examiner—John J. Calvert
Assistant Examiner—Robert H. Muromoto
(74) Attorney, Agent, or Firm—Pauley Petersen & Erickson

(57) ABSTRACT

A swimwear garment having a material which is permeable to liquid but substantially impermeable to bowel movement material. In one embodiment, the garment can comprise a stand-alone disposable pant liner in the form of a swimpant with waist elastics and leg elastics. In other embodiments, a mesh liner can be a layer within a disposable swimpant. The mesh liner can be attached to the disposable swimpant around the perimeter of the composite structure, or in swimpants containing containment flaps, to the containment flaps. The mesh liner can, optionally, further include elastic strands attached under the mesh liner to provide further lift and hold the mesh liner close to the body of the wearer.

23 Claims, 16 Drawing Sheets

U.S. PATENT DOCUMENTS

| | | | |
|---|---|---|---|
| 5,690,628 A * | 11/1997 | Huskey et al. | 604/390 |
| 5,776,122 A * | 7/1998 | Faulks et al. | 604/385.19 |
| 5,792,132 A | 8/1998 | Garcia | |
| 5,853,403 A | 12/1998 | Tanzer et al. | |
| 6,156,020 A | 12/2000 | Roe et al. | |
| 6,302,871 B1 * | 10/2001 | Nakao et al. | 604/385.13 |
| 6,307,120 B1 * | 10/2001 | Glaug | 604/383 |
| 6,395,115 B1 * | 5/2002 | Popp et al. | 156/66 |
| 6,402,731 B1 * | 6/2002 | Suprise et al. | 604/391 |
| 6,540,857 B1 * | 4/2003 | Coenen et al. | 156/163 |
| 6,572,601 B1 * | 6/2003 | Suprise et al. | 604/391 |
| 6,579,275 B1 * | 6/2003 | Pozniak et al. | 604/390 |
| 6,582,412 B1 * | 6/2003 | Christoffel et al. | 604/385.01 |
| 6,596,920 B1 * | 7/2003 | Wehner et al. | 604/364 |

FOREIGN PATENT DOCUMENTS

| | | |
|---|---|---|
| EP | 0 098 512 B1 | 11/1988 |
| EP | 0 382 022 A3 | 1/1990 |
| EP | 0 382 022 B1 | 1/1994 |
| EP | 0 717 971 A1 | 6/1996 |
| EP | 1 092 355 A1 | 4/2001 |
| EP | 1 110 463 A2 | 6/2001 |
| FR | 2 690 316 A1 | 10/1993 |
| GB | 2 268 073 A | 1/1994 |
| GB | 2 284 550 A | 6/1995 |
| WO | 00/00150 | 1/2000 |

* cited by examiner

PERMEABLE, CLOSE TO THE BODY LINER FOR SWIMWEAR

BACKGROUND OF THE INVENTION

This invention is directed to disposable swimpants and swimsuits for incontinent adults and children. More particularly, the swimpants include a material which is permeable to fluid, but substantially impermeable to larger bowel movement material.

For example, disposable swimpants and swimsuits for pre-toilet trained children usually have absorbent cores and moisture barriers to prevent leaks of urine and bowel movements. When a child swims while wearing a disposable swimpant, water gets inside the swimpant. One potential problem is that if bowel movement material is also inside the swimpant, when the child leaves the water, or stands up above the surface of the water, water will exit the swimpant through the leg openings and/or the waist opening and the bowel movement material may also exit along with the water, thus creating a sanitation problem. Even if the disposable swimpant has containment flaps, the bowel movement material could conceivably exit the swimpant along with the water through the leg openings and/or waist opening.

Another possible problem is that sand may end up within the swimpants and swimsuits of children at the beach. The sand can be an irritant to the skin and uncomfortable to the wearer. However, currently available disposable swimwear is not designed to allow sand to move away from direct contact with the wearer's skin.

There is a need or desire for a swimwear garment that provides bowel movement containment before and after swimming and also allows sand to move away from direct contact with the wearer's skin.

SUMMARY OF THE INVENTION

The present invention is directed in one embodiment to a swimwear garment, such as a swimpant, which is permeable to fluid but substantially impermeable to bowel movement material.

In one embodiment of the invention, the garment includes a stand-alone disposable pant liner. The stand-alone disposable pant liner is not attached to a conventional disposable swimpant. The stand-alone disposable pant liner is permeable to fluids and is impermeable to bowel movement material. The garment including the stand-alone disposable pant liner can be fastened at the sides with conventional hook and loop fasteners, or ultrasonically bonded at the sides, to form a one-piece pant. The garment including the stand-alone disposable pant liner can also have conventional waist and leg elastics. The stand-alone disposable pant liner can be made of a material that maintains its shape throughout vigorous activity, as well as when it gets wet. The stand-alone disposable liner can be worn underneath any conventional cloth swimwear. In particular embodiments, the stand-alone disposable pant liner may be made of a mesh material, the hole size of which may be selected so that it is permeable to fine particulates, such as sand.

In another embodiment of the invention, a mesh liner can be a layer within a disposable swimpant. The mesh liner in this embodiment can be positioned closest to the body of the wearer and on top of the body side liner. The disposable swimpant to which the mesh liner is attached may or may not have containment flaps. When the swimpant does not have containment flaps, the mesh liner can be attached to the disposable swimpant around the perimeter of the disposable swimpant so that the mesh liner can be detached from the majority of the absorbent portion of the swimpant. When the disposable swimpant does have containment flaps, the mesh liner can be attached to the containment flaps so that the mesh liner can be detached from the majority of the absorbent portion of the swimpant. In either of these embodiments, with or without the containment flaps, the center of the mesh liner is loose and freed up to be close to the body of the wearer.

In another embodiment of the invention, the mesh liner can be a layer within a disposable swimpant as described above and the mesh liner also can have elastic strands attached underneath the mesh liner parallel to the leg elastics. The elastic strands are designed to maintain contact with the body of the wearer and to keep the mesh liner close to the body of the wearer. The elastic strands also help to create a pocket within the mesh liner between the elastic strands to hold bowel movement material.

Prior to swimming, in the embodiment in which a mesh liner is a layer within a disposable swimpant, the garment can contain urine and bowel movements like a typical diaper or training pant. When the garment is worn before or while swimming, larger bowel movement material is kept inside the garment, specifically within the mesh liner, because the mesh liner of the invention is substantially impermeable to larger bowel movement material. In addition, any sand within the swimpant from before or after swimming will pass through the mesh liner. In this way, sand will not stay in direct contact with the wearer's skin.

With the foregoing in mind, it is a feature and advantage of one embodiment of the invention to provide a stand-alone disposable pant liner in the form of a swimpant that is permeable to liquid, but substantially impermeable to bowel movement material.

It is also a feature and advantage of one embodiment of the invention, to provide a mesh liner, which is permeable to liquid and sand, but substantially impermeable to bowel movement material, as a layer in a disposable swimpant.

It is also a feature and advantage of one embodiment of the invention to provide a mesh liner which is permeable to liquid and sand, but substantially impermeable to bowel movement material, as a layer in a disposable swimpant wherein the mesh liner additionally has elastic strands attached to its underside.

DEFINITIONS

Within the context of this specification, each term or phrase below will include the following meaning or meanings.

"Attached" refers to the joining, adhering, connecting, bonding, or the like, of at least two elements. Two elements will be considered to be attached to one another when they are attached directly to one another or indirectly to one another, such as when each is directly connected to intermediate elements.

"Airlaid" refers to a process for making material wherein fibers, such as cellulose-type fibers, are arranged on a wire where they are sprayed with an adhesive. The airlaid material is thus an adhesive-bonded material.

"Coform" refers to a material including a blend of natural fibers and/or synthetic polymer fibers.

"Dispersible" and "dispersibility" refer to the ability of a substance or structure to scatter or separate particles, such as water particles, into various directions. For example, partial dispersibility refers to scattering some, but not all, random particles of a substance into various directions; whereas selective dispersibility refers to scattering certain select particles into various directions.

"Elastic," "elasticized" and "elasticity" mean that property of a material or composite by virtue of which it tends to recover its original size and shape after removal of a force causing a deformation.

"Film" refers to a thermoplastic film made using a film extrusion and/or foaming process, such as a cast film or blown film extrusion process. The term includes apertured films, slit films, and other porous films which constitute liquid transfer films, as well as films which do not transfer liquid.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

"Layer" when used in the singular can have the dual meaning of a single element or a plurality of elements.

"Liquid-impermeable," when used to describe a layer or laminate means that liquid such as urine will not pass through the layer or laminate under ordinary use conditions in a direction generally perpendicular to the plane of the layer or laminate at the point of liquid contact.

"Liquid-permeable," refers to a layer or laminate that is not liquid-impermeable.

Figure 6A:
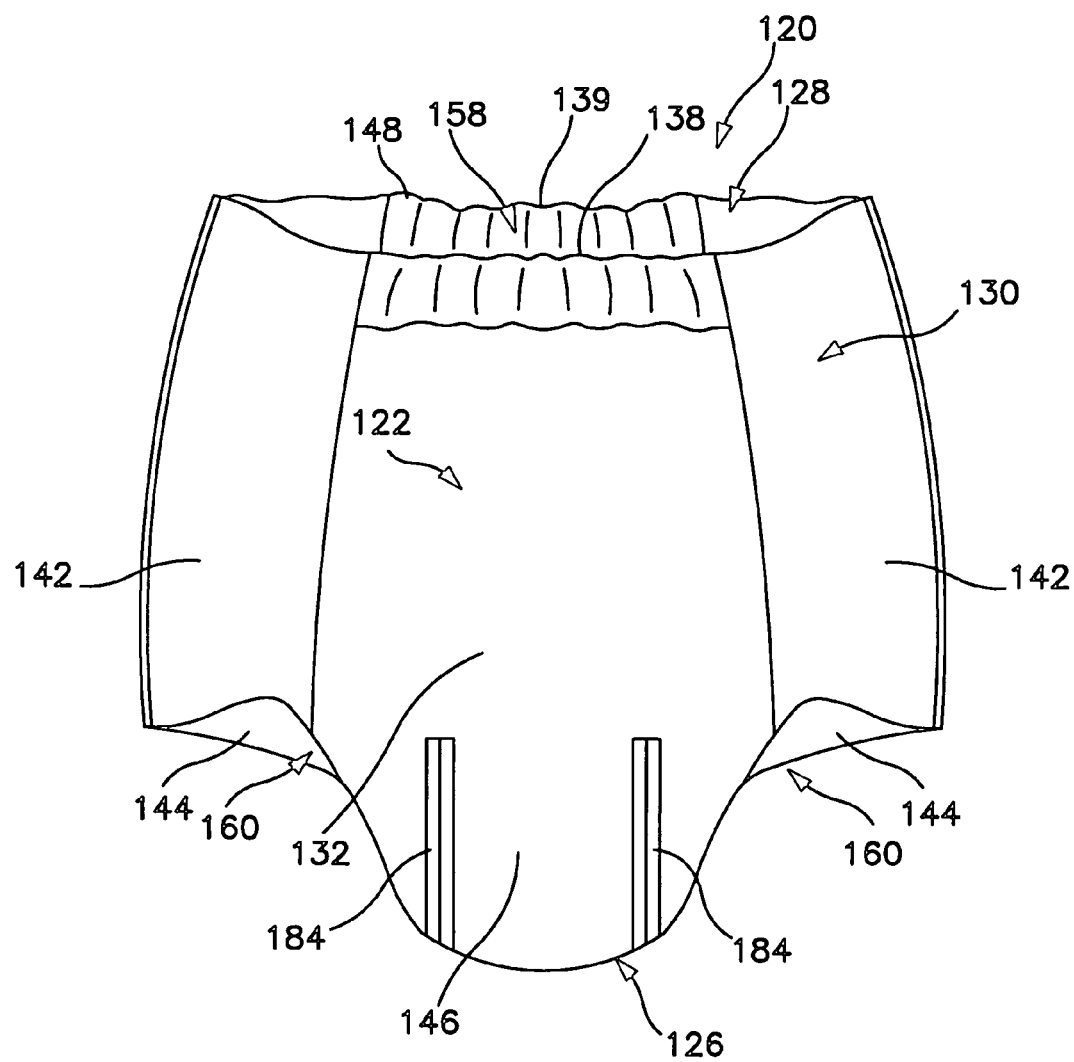
FIG. 6A is a front perspective view of another embodiment of the invention, a disposable swimpant including a mesh liner, (mesh liner not visible)
Figure 6B:
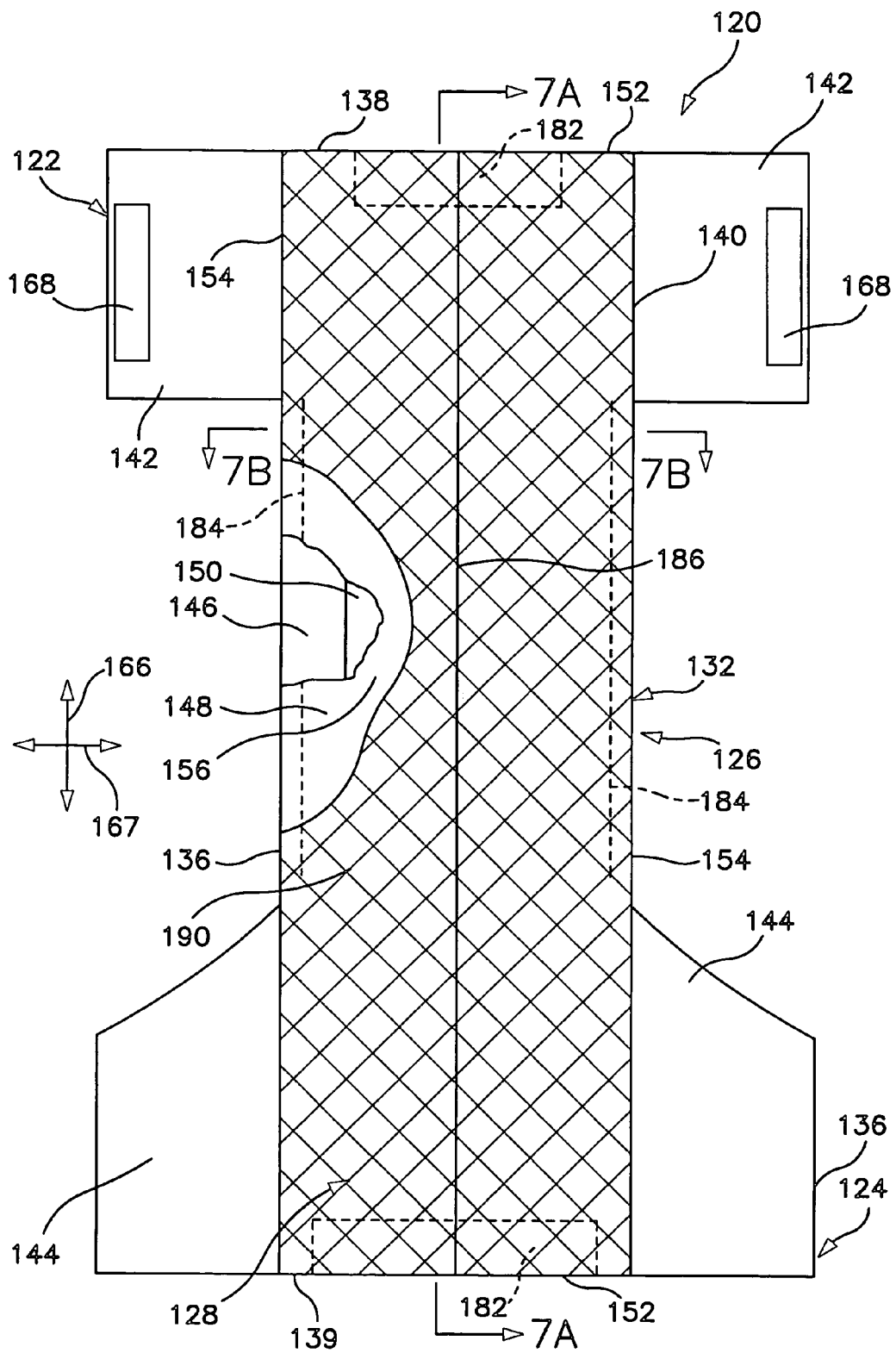
FIG. 6B is a plan view of the embodiment of FIG. 6A, showing the mesh liner attached to the swimpant, shown in a partially disassembled, stretched flat state, and showing the surface of the swimpant that faces the wearer when the swimpant is worn, and with portions cut away to show the underlying features.

"Longitudinal" and "transverse" have their customary meaning, as indicated by the longitudinal and transverse axes depicted in FIG. 6B. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self-bonding when deposited onto a collecting surface. Meltblown fibers used in the present invention are preferably substantially continuous in length.

"Mesh" refers to a material that has the ability to allow fluid and particulates of a specific size range to filter through. This can be accomplished by mechanical means (e.g., pin roll aperturing) or the process by which to make the material (hydroentangling, meltblowing, spunbonding). The material has an open network that allows fluid or particulates of a specific size to pass through it.

"Nonwoven material" refers to a web or fabric having a structure of individual fibers or threads which are interlaid, but not in an identifiable manner as in a knitted fabric. Nonwoven webs or fabrics have been formed from many processes, such as, for example, meltblowing processes, spunbonding processes, and bonded carded web processes. In particular embodiments, nonwoven fabrics as utilized in the present invention are produced from polymers, such as, for example, polyethylene or polypropylene.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Stand-alone," as used herein to describe a pant liner, means that the pant liner exists as an independent product, divorced from all substantially absorbent materials, and divorced from any layers that would make the pant liner substantially liquid impermeable. For example, a stand-alone liner includes no fluff or superabsorbent material, and includes no liquid impermeable plastic film layers covering a majority of the product. "Stand-alone" does not exclude features such as waist elastic, leg elastic, crotch elastic, containment flaps, fasteners, or the like.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

"Thermoplastic" describes a material that softens when exposed to heat and which substantially returns to a non-softened condition when cooled to room temperature.

"Z-fold" is used to describe a folding of a material back upon itself twice, in opposite directions, as may generally be seen in, or defined by, the shape of a letter "Z".

These terms may be defined with additional language in the remaining portions of the specification.

DETAILED DESCRIPTION OF THE PRESENTLY PREFERRED EMBODIMENTS

The present invention is directed to a swimwear garment including a material which is permeable to liquid, but substantially impermeable to bowel movement material.

The material of the present invention can include a stand-alone disposable pant-liner, or can be incorporated into disposable, pant-like, swimwear articles, such as swimpants and swimsuits.

FIGS. 1–5 each illustrate an embodiment of the invention, namely a stand-alone disposable pant liner. The stand-alone disposable pant liner 20 can include a liquid-permeable material 21, can be a single layer or a double layer of material, or can include additional layers. The stand-alone disposable pant liner 20 includes a chassis 22 defining a front region 24, a back region 26, a crotch region 28 interconnecting the front and back regions, an inner surface 30 which is configured to contact the wearer, and an outer surface 32 opposite the inner surface. The inner surface 30 faces the wearer when the garment is worn. As shown, the chassis 22 also defines a pair of longitudinally opposed waist edges, which are designated front waist edge 34 and back waist edge 36. The front region 24 is contiguous with the front waist edge 34, and the back region 26 is contiguous with the back waist edge 36.

Figure 1:
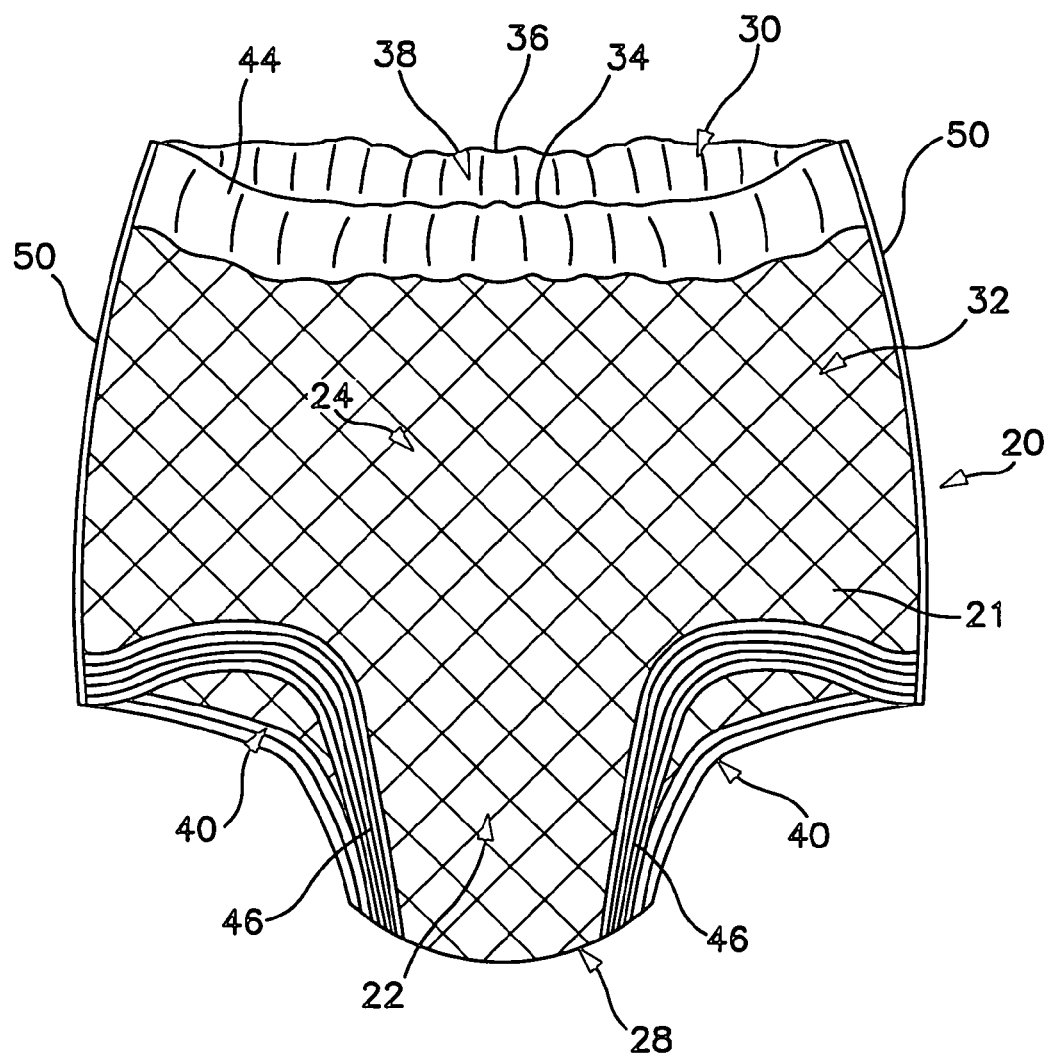
FIG. 1 is a front perspective view of one embodiment of the invention, a mesh liner as a swimpant with curved leg elastics.
Figure 2:
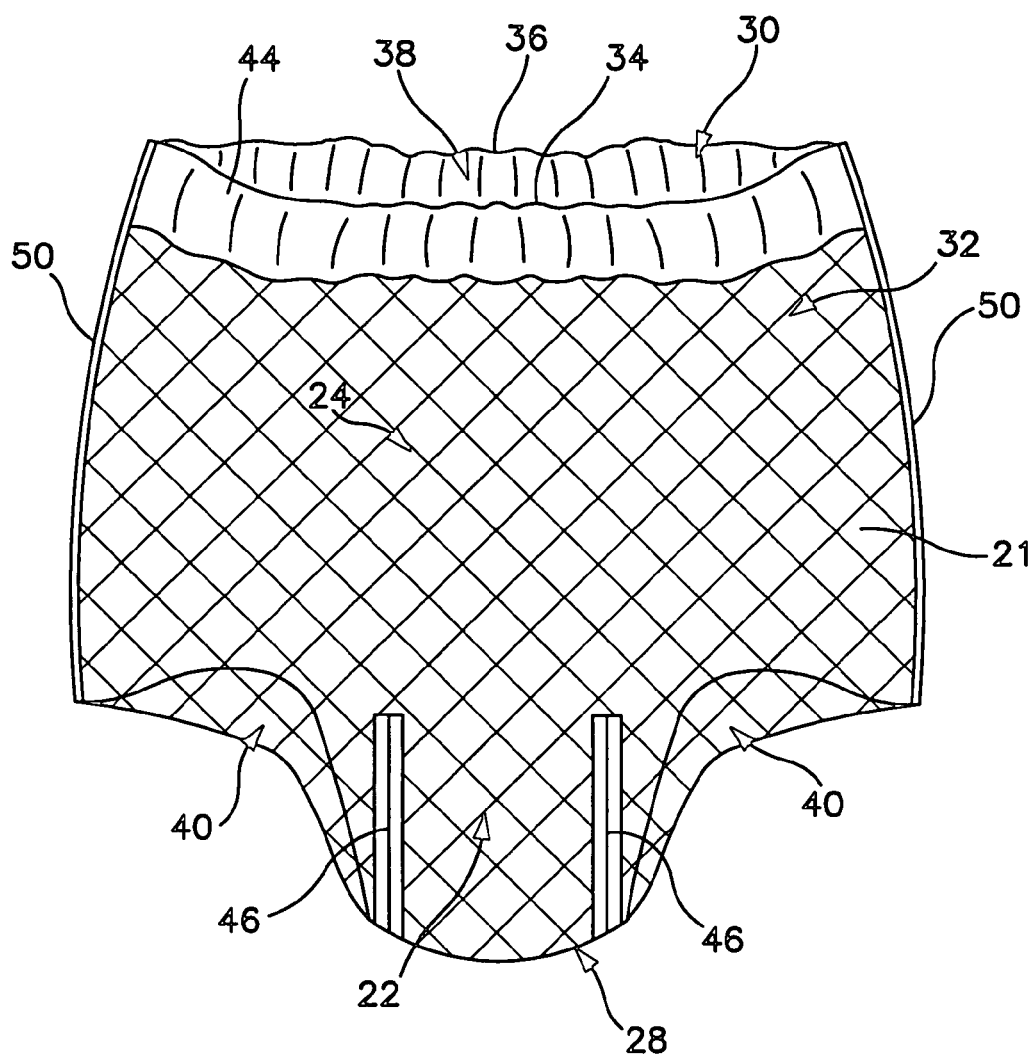
FIG. 2 is a front perspective view of a mesh liner as a swimpant with straight leg elastics.
Figure 3:
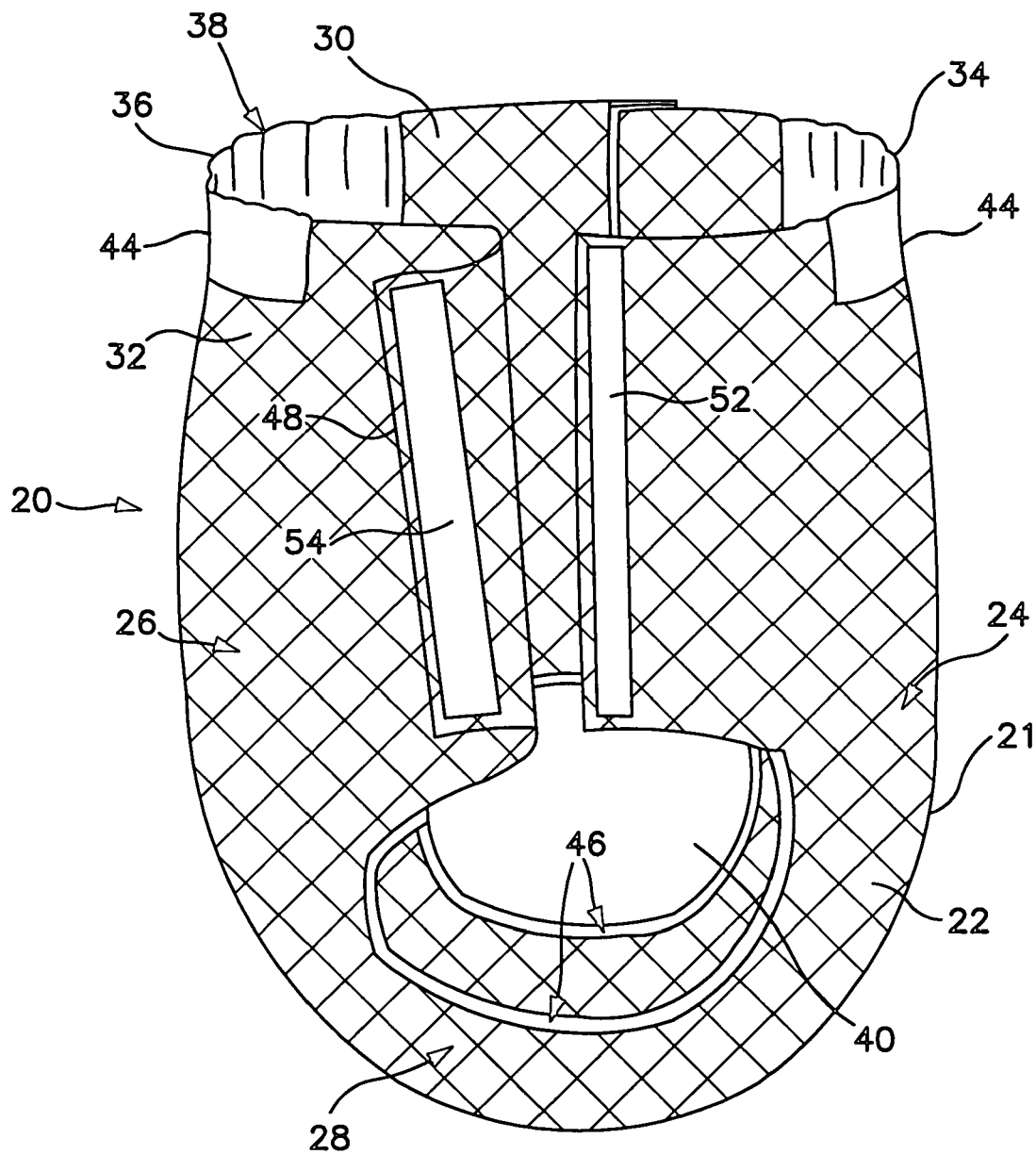
FIG. 3 is a side perspective view of a mesh liner as a swimpant with a fastening system.

As shown in the stand-alone disposable pant liner 20 in FIGS. 1–3, in particular embodiments the front and back regions 24 and 26 together define a three-dimensional pant configuration having a waist opening 38 and a pair of leg openings 40. The waist edges 34 and 36 of the chassis 22 are configured to encircle the waist of the wearer when worn and provide the waist opening 38 which defines a waist perimeter dimension. Portions of the transversely opposed side edges 42 (FIGS. 4 and 5) in the crotch region 28 generally define the leg openings 40. The front region 24 includes the portion of the stand-alone disposable pant liner 20 which, when worn, is positioned on the front of the wearer while the back region 26 includes the portion of the stand-alone disposable pant liner 20 which, when worn, is positioned on the back of the wearer. The crotch region 28 of the stand-alone disposable pant liner 20 includes the portion of the stand-alone disposable pant liner 20 which, when worn, is positioned between the legs of the wearer and covers the lower torso of the wearer.

Figure 4:
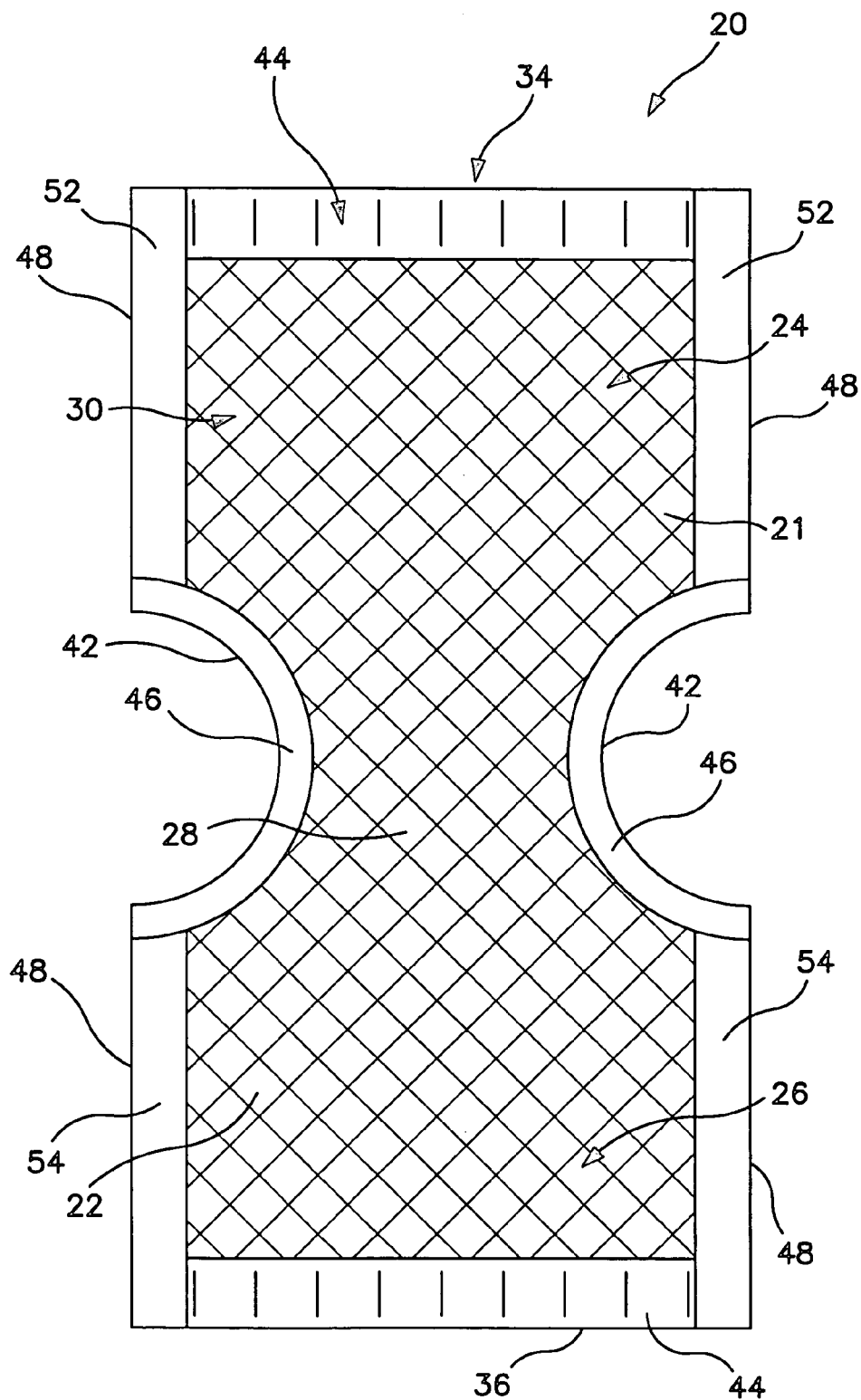
FIG. 4 is a plan view of a mesh liner as a swimpant with curved leg elastics in a stretched flat state, and showing the surface of the swimpant that faces the wearer when the swimpant is worn.

To further enhance containment of bowel movement material, the stand-alone disposable pant-liner 20 can include waist elastic members 44 and/or leg elastic members 46, as are known to those skilled in the art. The waist elastic members 44 can be operatively joined to the mesh liner, and can extend over part (FIG. 3) or all (FIGS. 1–2, 4–5) of the waist edges 34, 36. The leg elastic members 46 can be operatively joined to the stand-alone disposable pant liner 20 along the side edges 42 to provide curved elastics (FIGS. 1, 4). The leg elastic members 46 can also be operatively joined to the mesh liner longitudinally along the opposite side edges 42 and positioned in the crotch region 28 of the stand-alone disposable pant liner 20 to provide straight leg elastics (FIGS. 2, 5A–5B).

Figure 5A:
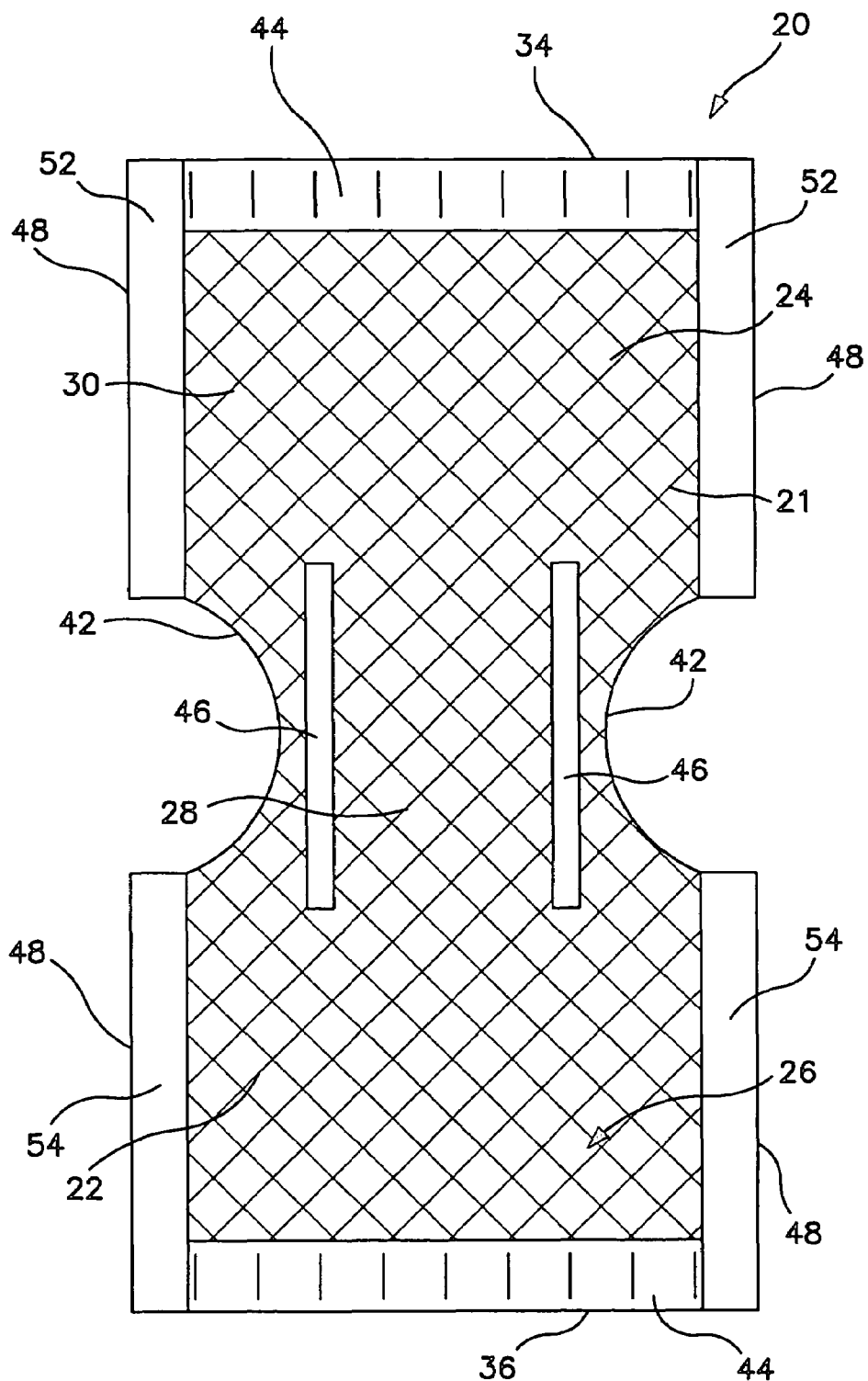
FIG. 5A is a plan view of a mesh liner as a swimpant with straight leg elastics in a stretched flat state, and showing the surface of the swimpant that faces the wearer when the swimpant is worn.
Figure 5B:
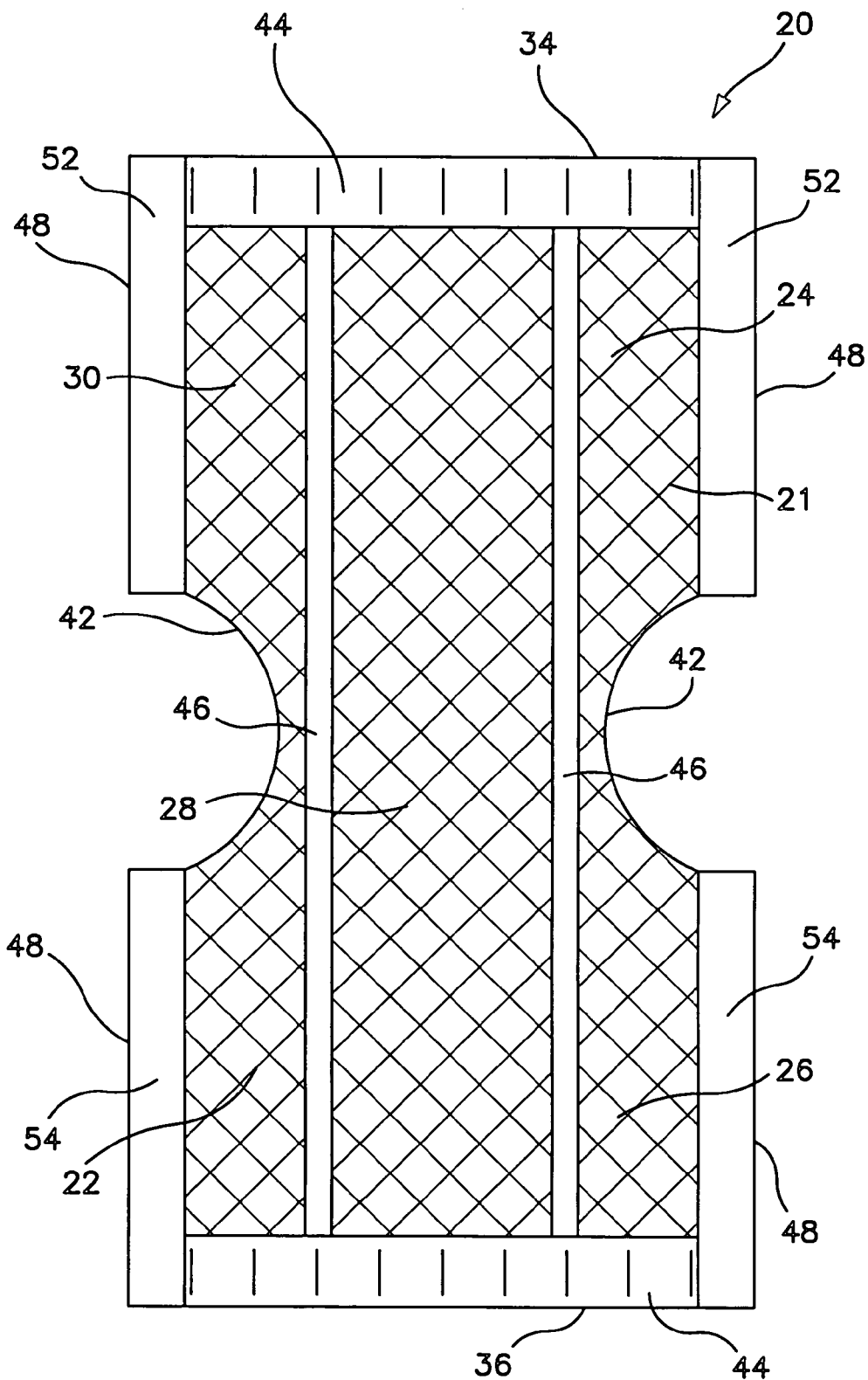
FIG. 5B is a plan view of a mesh liner as a swimpant in a stretched flat state, with straight leg elastics running the full length of the mesh liner, and showing the surface of the swimpant that faces the wearer when the swimpant is worn.

The straight leg elastic members 46 may run along only part of the length of the stand-alone disposable pant liner 20, as shown in FIG. 5A. Alternatively, the straight-leg elastic members 46 may run the full length of the stand-alone disposable pant liner 20, as shown in FIG. 5B. In particular embodiments, the stand-alone disposable pant liner 20 can, although not necessarily, include a pair of containment flaps. Suitable constructions and arrangements for the containment flaps are generally well known to those skilled in the art and are described in U.S. Pat. No. 4,704,116 issued Nov. 3, 1987 to Enloe, which is incorporated herein by reference.

The waist elastic members 44 and the leg elastic members 46 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the waist elastic members 44 and/or the leg elastic members 46 include a plurality of dry-spun coalesced multifilament spandex elastomeric threads sold under the trade name LYCRA® and available from E.I. du Pont de Nemours and Company, Wilmington, Del., U.S.A. In another particular embodiment, for example, the waist elastic members 44 and/or the leg elastic members 46 can include Findley HX 2695-01 adhesive laminated to two facings of 0.6 osy bicomponent polypropylene/polyethylene spunbond. Alternatively, six strands of 310 decitex LYCRA® can be also laminated at 250% elongation between the spunbond facings in addition to the Findley adhesive.

The side edges 48 of the chassis 22 can be suitably joined together, such as by ultrasonic bonding, to form side seams 50 extending from the waist opening 38 to the leg openings 40 (FIGS. 1 and 2). The provision of side seams 50 can be accomplished in the manner described in U.S. Pat. No. 5,046,272, issued Sep. 10, 1991 to Vogt et al., which is incorporated herein by reference.

Alternatively, the side edges 48 of the chassis can be releasably attached to one another by a fastening system extending from the waist opening 38 to the first and second leg openings 40. The illustrated fastening system includes fastening components 52 that are adapted to refastenably connect to mating fastening components 54 (FIG. 3). In one embodiment, one surface of each of the fastening components 52 and 54 includes a plurality of engaging elements that project from that surface. The engaging elements of these fastening components 52 are adapted to repeatedly engage and disengage the engaging elements of the mating fastening components 54.

Also, the side edges 48 need not be prefastened or prebonded. In other words, the stand-alone disposable pant liner 20 need not be provided in a pant-like configuration, but can, rather, be provided in a flat configuration.

In one particular embodiment, the fastening components 52 each include hook type fasteners and the mating fastening components 54 each include complementary loop type fasteners. In another particular embodiment, the fastening components 52 each include loop type fasteners and the mating fastening components 54 each include complementary hook type fasteners. The fastening components 52 and the mating fastening components 54 are desirably rectangular, although they can alternatively be square, round, oval, curved or otherwise non-rectangularly shaped.

Loop type fasteners typically include a fabric or material having a base or backing structure and a plurality of loop members extending upwardly from at least one surface of the backing structure. The loop material can be formed of any suitable material, such as acrylic, nylon or polyester, and can be formed by methods such as warp knitting, stitch bonding or needle punching. Suitable loop materials are available from Guilford Mills, Inc., Greensboro, N.C., U.S.A. under the trade designation No. 36549.

Hook type fasteners typically include a fabric or material having a base or backing structure and a plurality of hook members extending upwardly from at least one surface of the backing structure. In contrast to the loop type fasteners which desirably include a flexible fabric, the hook material advantageously includes a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material can be molded or extruded of nylon, polypropylene or another suitable material. An example of suitable single-sided hook materials for the fastening components 52 or the mating fastening components 54 is available from Velcro Industries B.V., Amsterdam, Netherlands or affiliates thereof, and are identified as Velcro HTH-829 with a uni-directional hook pattern and having a thickness of about 0.089 millimeters (3.5 mils) and HTH-851 with a uni-directional hook pattern and having a thickness of about 0.051 millimeters (2 mils).

The stand-alone disposable pant liner 20 of the present invention can be worn under traditional cloth swimwear and/or under other commercially available swimwear, such as disposable training pants.

The stand-alone disposable pant liner 20 can be made of nonwoven materials, such as spunbond polypropylene or spunbond polyethylene, or a spunbond stretch thermal laminate, or a spunbond/meltblown/spunbond (SMS) web combination. The stand-alone disposable pant liner can also be made of nylon, or any other material having the desired permeability, durability, and cost characteristics.

In particular embodiments, the material used for the stand-alone disposable pant liner 20 can be a mesh material. The mesh material has a basis weight of about 7 gsm (0.2 osy) to about 85 gsm (2.5 osy), suitably about 14 gsm (0.4 osy) to about 54 gsm (1.6 osy), or alternatively, about 20 gsm (0.6 osy) to about 41 gsm (1.2 osy). The mesh material also has a hole size of about 147.3 microns to about 5810 microns. Therefore, the mesh material is permeable to liquid and fine particulates, such as sand, but substantially impermeable to bowel movement materials. The mesh material can be either a single layer or double layer of material, or can include additional layers. As used herein, "substantially impermeable to bowel movement materials" means that the mesh material is impermeable to solid bowel movement material, but the mesh material can be permeable to bowel movement material that is loose, or not solid.

In addition, the mesh material has a tensile strength of at least about 5 pounds of force per 4 inches of material, suitably at least about 10 pounds of force per 4 inches of material, at least about 13 pounds of force per 4 inches of material or alternatively, at least about 19 pounds of force per 4 inches of material. Suitable mesh materials can be made from nonwoven materials such as 0.6 osy (ounces per square yard) spunbond material apertured with a pin diameter size of 0.081 inches. Such materials can be made by Kimberly-Clark Corporation in Lexington, N.C., U.S.A.

The stand-alone disposable pant liner 20 is substantially free of absorbent material and substantially free of liquid-impermeable materials.

Another embodiment of the present invention is directed to a disposable swimwear garment having a mesh liner, as described in detail above. The principles of this embodiment can be incorporated into disposable, pant-like, swimwear articles, such as swimpants and swimsuits. The garment of this embodiment may, but need not have absorbent characteristics. For ease of explanation, the following description is in terms of a child absorbent swimpant.

Referring to FIGS. 6A and 6B, disposable swimpant 120 is illustrated. The swimpant 120 includes an absorbent chassis 132 defining a front region 122, a back region 124, a crotch region 126 interconnecting the front and back regions, an inner surface 128 which is configured to contact the wearer, and an outer surface 130 opposite the inner surface which is configured to contact a swimming environment, such as a pool or lake.

Figure 8A:
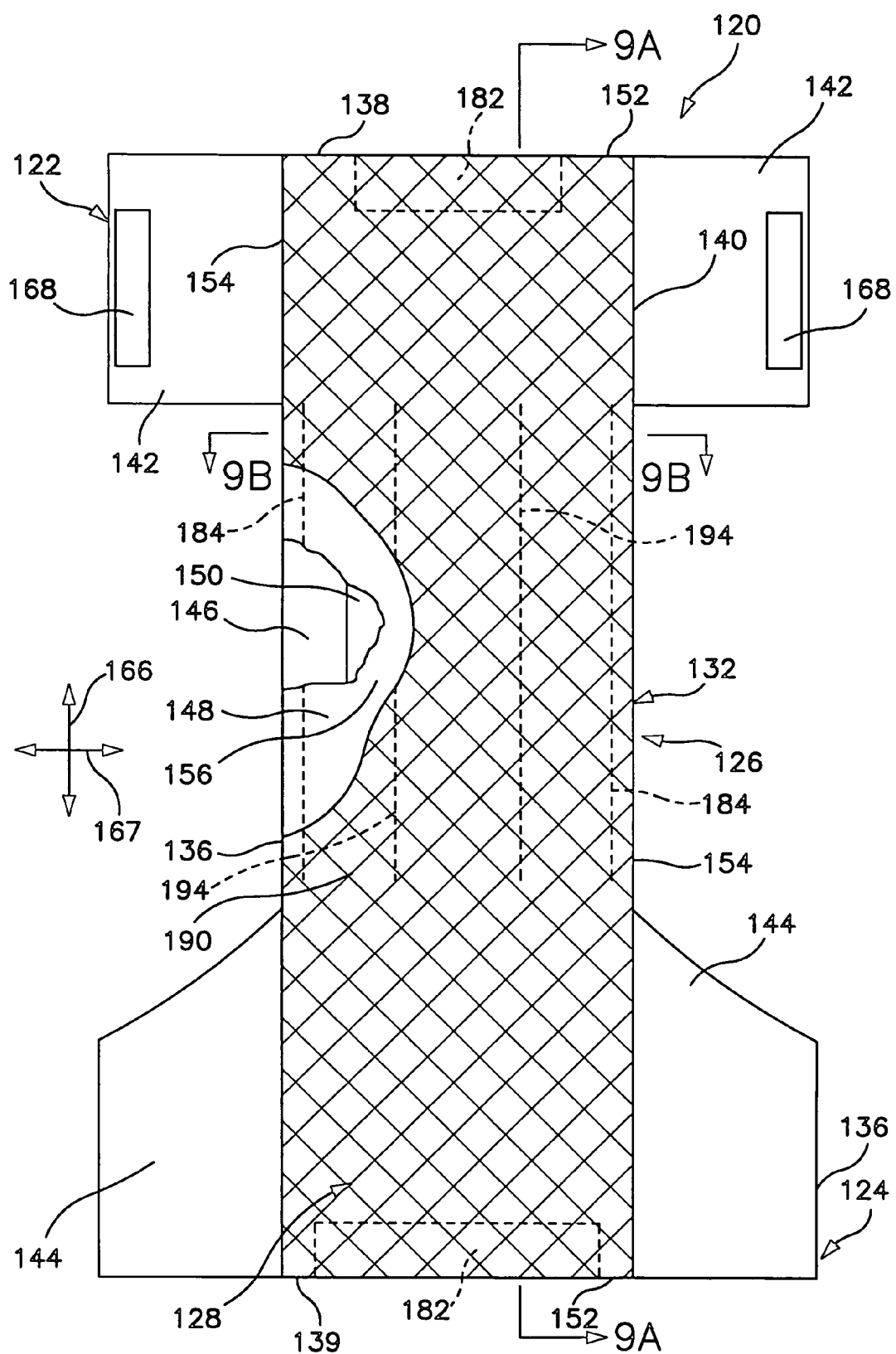
FIG. 8A is a plan view of another embodiment of the invention, a mesh liner attached to a swimpant, shown in a partially disassembled, stretched flat state, with elastic strands attached underneath the mesh liner, and showing the surface of the swimpant that faces the wearer when the swimpant is worn, and with portions cut away to show the underlying features.
Figure 10:
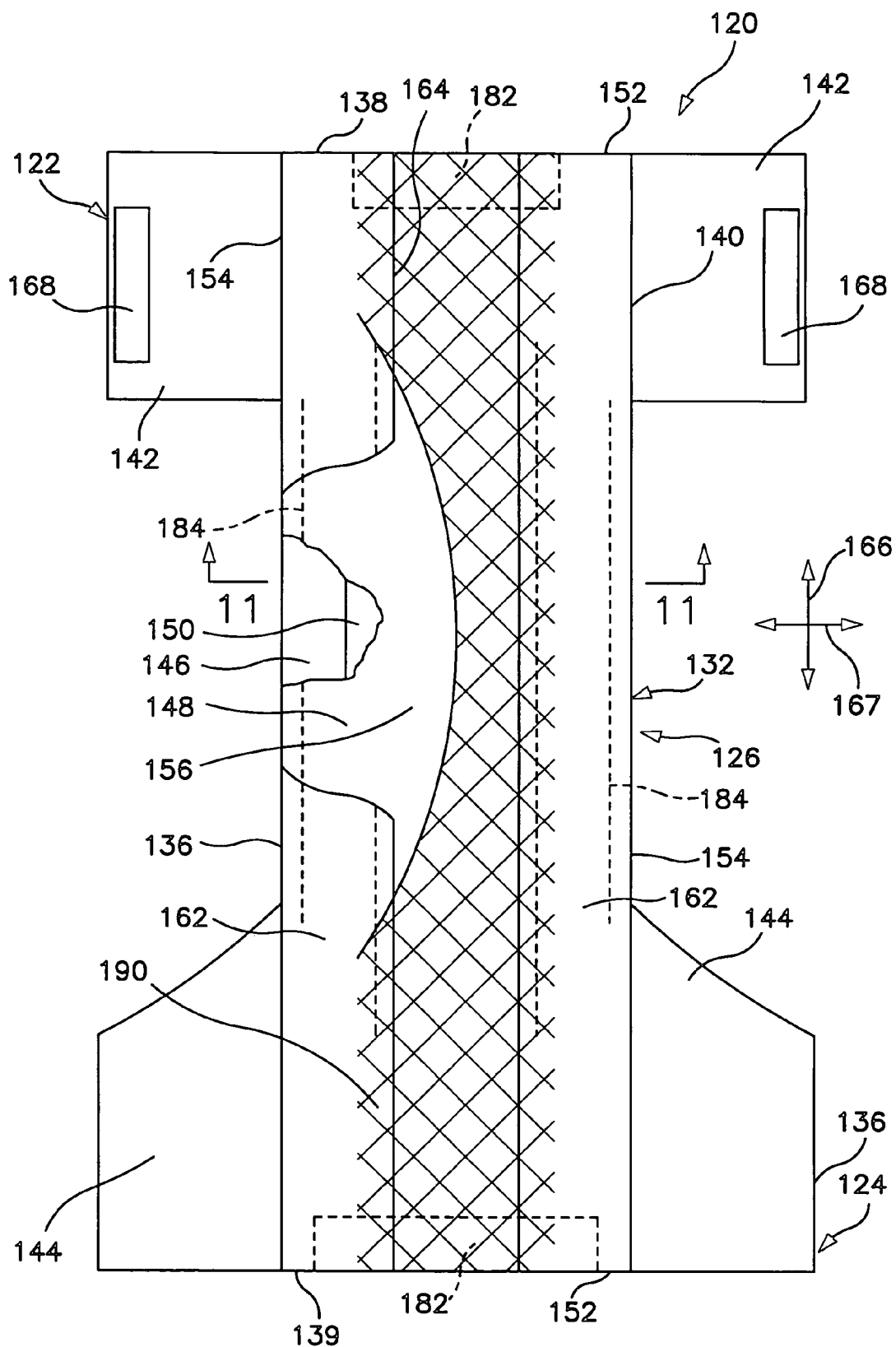
FIG. 10 is a plan view of yet another embodiment of the invention, a mesh liner attached to a swimpant, shown in a partially disassembled, stretched flat state, having containment flaps, and showing the surface of the swimpant that faces the wearer when the swimpant is worn, and with portions cut away to show the underlying features.

Referring to FIG. 6B, the swimpant 120 is shown in a partially disassembled, stretched flat state, showing the inner surface 128 which faces the wearer when the garment is worn. As shown, the absorbent chassis 132 also defines a pair of transversely opposed side edges 136 and a pair of longitudinally opposed waist edges, which are designated front waist edge 138 and back waist edge 139. The front region 122 is contiguous with the front waist edge 138, and the back region 124 is contiguous with the back waist edge 139. The chassis 132 also includes a somewhat rectangular composite structure 140, a pair of transversely opposed front side panels 142, and a pair of transversely opposed back side panels 144. The composite structure 140 and side panels 142 and 144 can be integrally formed, or can include two or more separate elements, as shown in FIGS. 6A and 6B. For reference, arrows 166 and 167 depicting the orientation of the longitudinal axis and the transverse axis, respectively, of the training pant 120 are illustrated in FIGS. 6B, 8A and 10.

The illustrated composite structure 140 includes an outer cover 146, a body side liner 148 which is connected to the outer cover 146 in a superposed relation, and an absorbent assembly 150 which is located between the outer cover 146 and the body side liner 148. The somewhat rectangular composite structure 140 has opposite linear end edges 152 that form portions of the front and back waist edges 138 and 139, and opposite linear, or curvilinear, side edges 154 that form portions of the side edges 136 of the absorbent chassis 132. The linear end edges 152 and the side edges 154 define a perimeter of the somewhat rectangular composite structure 140 as well as a central region 156 within the perimeter of the somewhat rectangular composite structure 140.

Figure 7A:
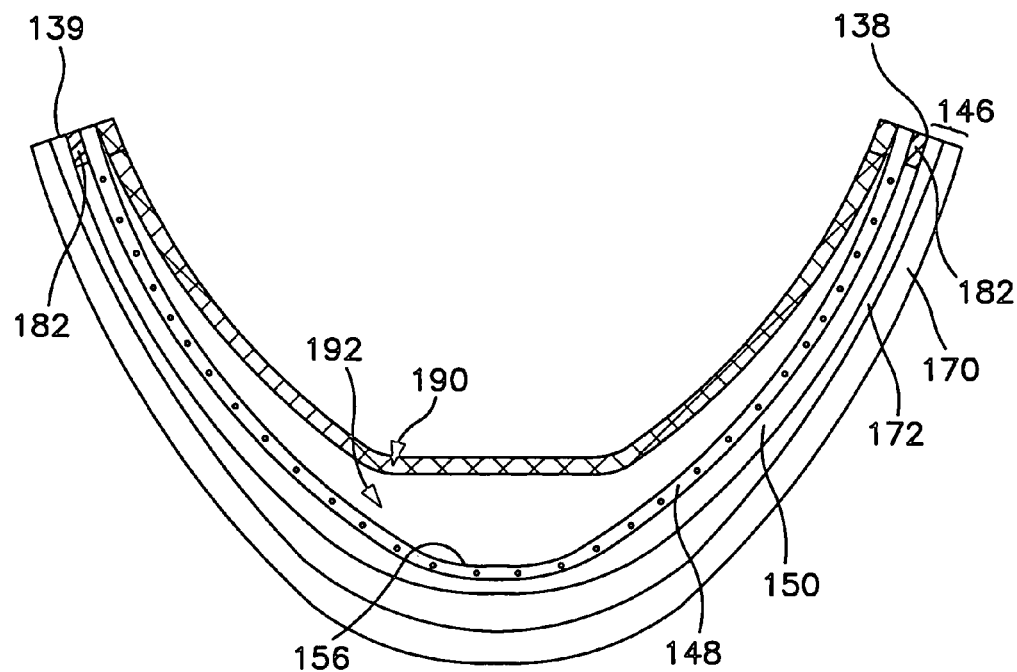
FIG. 7A is a cross-sectional view of FIG. 6B along line 7A—7A, when the swimpant has been folded up slightly so that a front waist edge approaches a back waist edge.
Figure 7B:
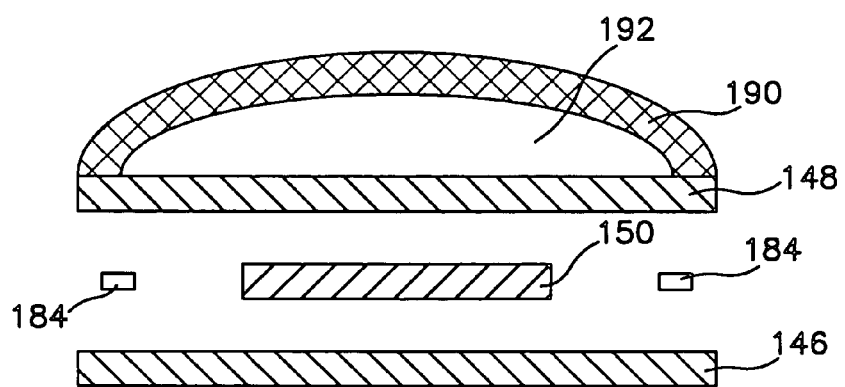
FIG. 7B is a cross-sectional view of FIG. 6B along line 7B—7B.

According to one embodiment of the present invention, the swimpant 120 further includes a mesh liner 190, made of the mesh material described above. The mesh liner 190 is attached to the composite structure 140 around the perimeter of the composite structure 140 on top of the body side liner 148 (FIG. 6B). The attachment of the mesh liner 190 around the perimeter of the composite 140 leaves an unattached space 192 between the mesh liner 190 and the body side liner 148, as shown in FIGS. 7A and 7B. By attaching the mesh liner 190 around the perimeter, instead of just to the liner end edges 152, if bowel movement particulate or liquid material does pass through the mesh liner 190 into the unattached space 192, the attachment of the mesh liner 190 to the liner side edges 154, which form part of the perimeter, acts as another barrier to the bowel movement material slipping out of the swimpant 120 completely.

The unattached space 192 lies over the central region 156 of the composite structure 140. In this way, the mesh liner 190 lies close to the body of the wearer. The mesh liner 190 can be attached around the perimeter of the composite structure by means of adhesives known to those skilled in the art. Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. Other suitable forms of bonding can be used to attach the mesh liner 190 to the composite structure 140 such as ultrasonic bonding, thermal bonding, sewing, or staples, or the like, as are known in the art.

The unattached space 192 allows fluid to flow more freely throughout the swimpant 120 as opposed to directly into the composite structure 140. The mesh liner 190 acts as a draining mechanism while separating the bowel movement material from the chassis 132. The unattached space 192 is not affected by the potential droop of the swimpant 120 in the crotch region 126 when the swimpant 120 gets wet. Thus, the mesh liner 190 can stay closer to the body of the wearer and keeps a tighter trap on any bowel movement material in the swimpant 120. Furthermore, the unattached space 192 allows sand to flow onto the composite structure 140 and potentially out of the swimpant 120. The mesh liner 190 serves to contain bowel movement material, and also to separate sand from the body of the wearer.

As shown in the swimpant 120 in FIG. 6A, the front and back regions 122 and 124 together define a three-dimensional pant configuration having a waist opening 158 and a pair of leg openings 160. The waist edges 138 and 139 of the absorbent chassis 132 are configured to encircle the waist of the wearer when worn and provide the waist opening 158 which defines a waist perimeter dimension. Portions of the transversely opposed side edges 136 (FIG. 6B) in the crotch region 126 generally define the leg openings 160. The front region 122 includes the portion of the swimpant 120 which, when worn, is positioned on the front of the wearer while the back region 124 includes the portion of the swimpant 120 which, when worn, is positioned on the back of the wearer. The crotch region 126 of the swimpant 120 includes the portion of the swimpant 120 which, when worn, is positioned between the legs of the wearer and covers the lower torso of the wearer.

Figure 8B:
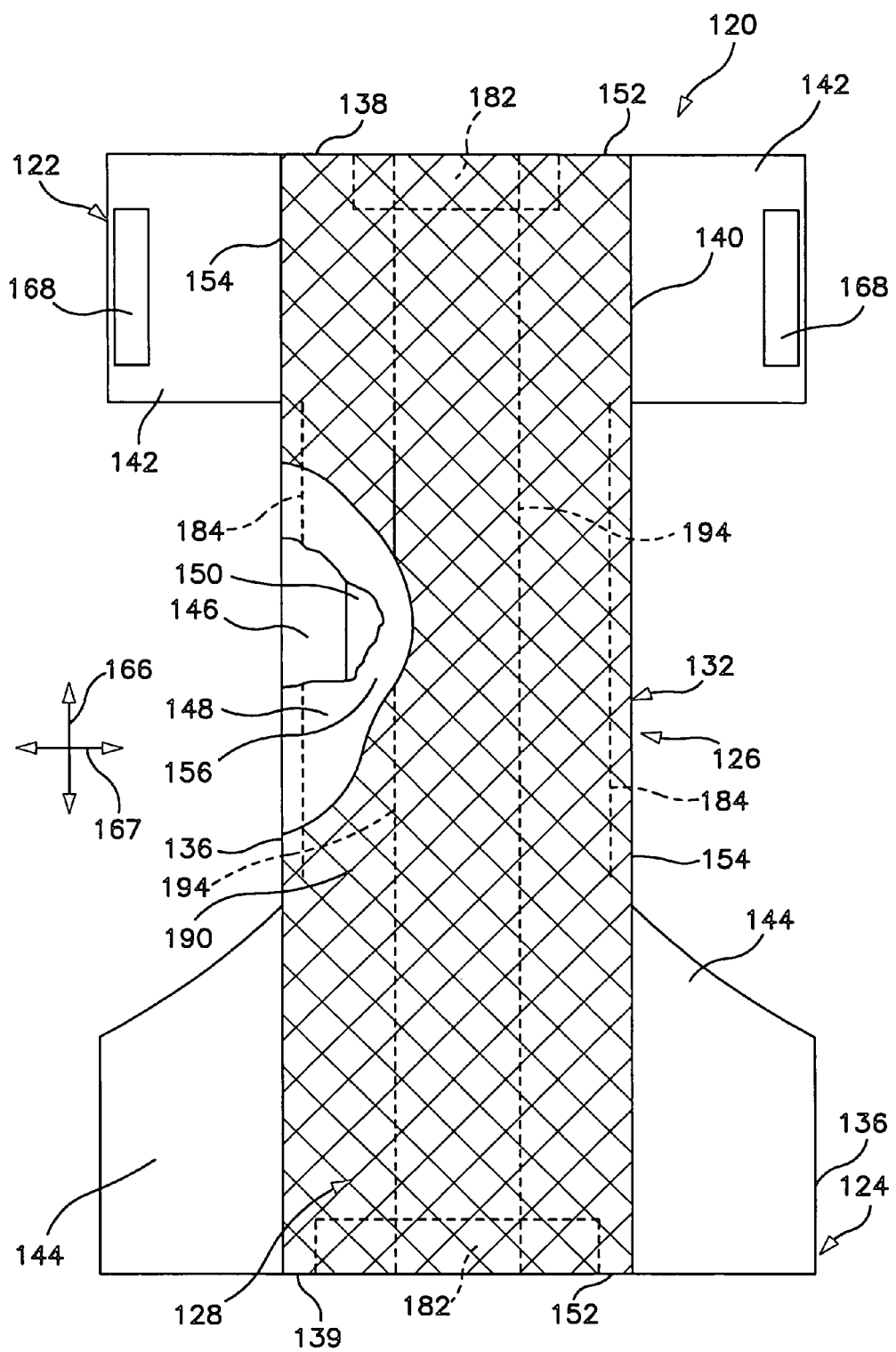
FIG. 8B is a plan view of another embodiment of FIG. 8A, showing the elastic strands running from the front waist edge to the back waist edge.
Figure 9A:
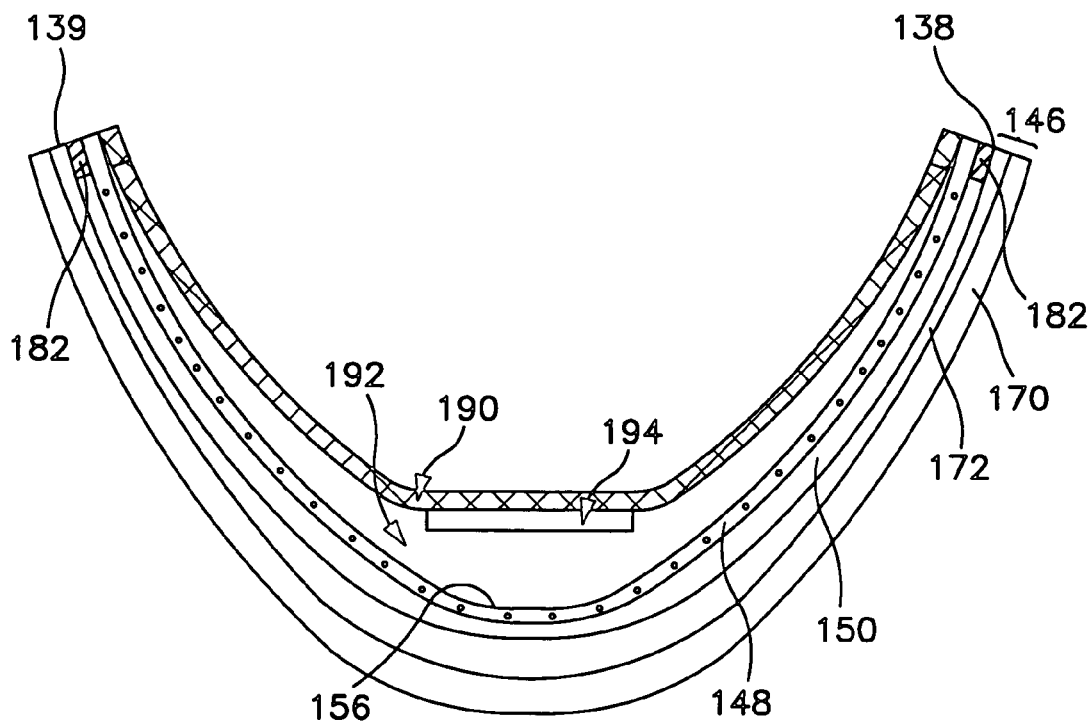
FIG. 9A is a cross-sectional view of FIG. 8A along line 9A—9A, when the swimpant has been folded up slightly so that a front waist edge approaches a back waist edge 39.
Figure 9B:
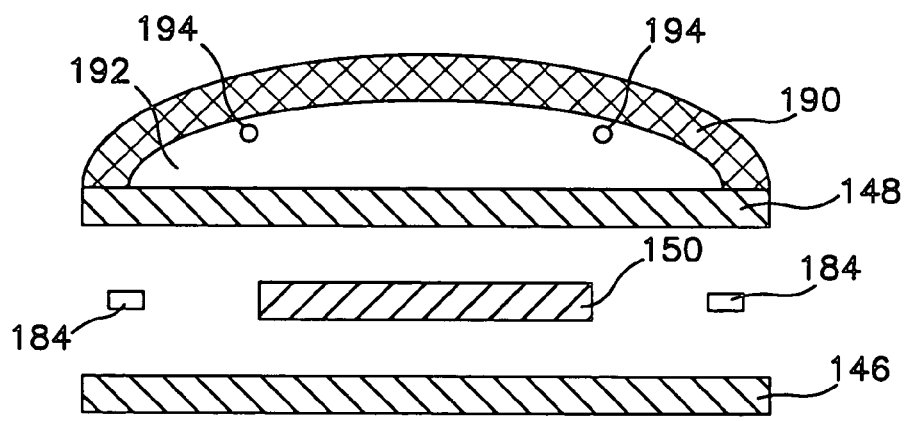
FIG. 9B is a cross-sectional view of FIG. 8A along line 9B—9B.

Referring to FIGS. 8A, 8B, 9A and 9B, in another embodiment of the invention, the mesh liner 190 can further include elastic strands 194 attached to an underneath portion of the mesh liner 190 adjacent the body side liner 148. In particular embodiments, the elastic strands 194 can be parallel to leg elastics 184. The elastic strands 194 provide additional lift to the mesh liner 190. As shown in FIGS. 9A and 9B, the size of the unattached space 192 is slightly larger than the corresponding unattached space 192 in the embodiment without elastic strands 194 shown in FIGS. 7A and 7B. In this way, the mesh liner 190 lies even closer to the body of the wearer. Any of the previously described elastic materials can be suitable the elastic strands 194.

The elastic strands 194 can run along only part of the length of the swimpant, for example, the same distance as the leg elastics 184, as shown in FIG. 8A. Alternatively, the elastic strands 194 can run the full length of the swimpant 120 from the front waist edge 138 to the back waist edge 139 as shown in FIG. 8B. The elastic strands 194 also help to create a pocket within the mesh liner between the elastic strands to hold bowel movement material. The elastic strands 194 also help to keep the mesh liner 190 tight to the body to minimize leakage potential.

The mesh liner 190 is permeable to fluid and to fine particulates such as sand, but substantially impermeable to larger particulates such as larger bowel movement material.

When a wearer wears absorbent swimwear of this embodiment of the invention into a swimming environment, the swimwear can become filled with water and bowel movement material. Therefore, the swimpant 120 of this invention substantially retains any bowel movement, or other non-particulate solid material within the mesh liner 190. The sand-permeability allows the sand to move away from direct contact with the wearer's skin, although may still be contained within the swimpant. The mesh liner 190 will permit the sand and other fine particulates to move from the area in direct contact with the wearer's skin through to the body side liner 148.

The absorbent chassis 132 can optionally be configured to contain and/or absorb any body exudates discharged from the wearer. For example, the absorbent chassis 132 can include a pair of elasticized containment flaps 162 (FIG. 10) attached to the side edges 154 of the composite structure 140. The containment flaps 162 are configured to provide a barrier to the transverse flow of body exudates. However, as previously mentioned, even with the presence of the containment flaps 162 in disposable swimpants without the mesh liner of the present invention, bowel movement material may still sometimes exit the swimpant 120 along with water through the leg openings 160 or the waist opening 158.

The elasticized containment flaps 162 define an unattached edge 164 which assumes an upright, generally perpendicular configuration in at least the crotch region 126 of the swimpant 120 to form a seal against the wearer's body. Suitable constructions and arrangements for the containment flaps 162 are generally well known to those skilled in the art and are described in U.S. Pat. No. 4,704,116 issued Nov. 3, 1987 to Enloe, which is incorporated herein by reference.

According to another embodiment of the present invention, the mesh liner 190 can be attached to the containment flaps. 162, as shown in FIG. 10. The mesh liner 190 can be attached on top of the containment flaps 162, while the containment flaps 162 are in a flat position and not attached to the central region 156 of the composite structure 140.

Figure 11A:
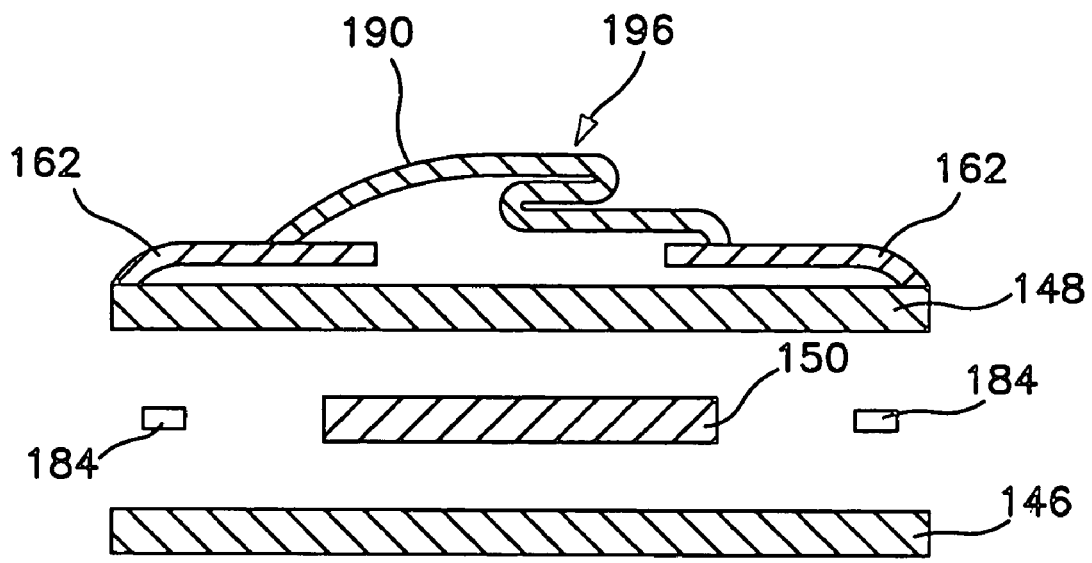
FIG. 11A is a cross-sectional view of FIG. 10 along line 11—11, showing a z-fold in the mesh liner attached to the containment flaps.

In this embodiment of the invention, in order to allow for the containment flaps 162 to move into the perpendicular position, as described above, the mesh liner 190 can be folded one or more times. For example, a z-fold 196 can be provided in the mesh liner 190 (FIG. 11A). Folding the mesh liner 190 provides slack in the mesh liner 190, to account for the movement of the containment flaps 162 into the perpendicular position (FIG. 11B).

Figure 11B:
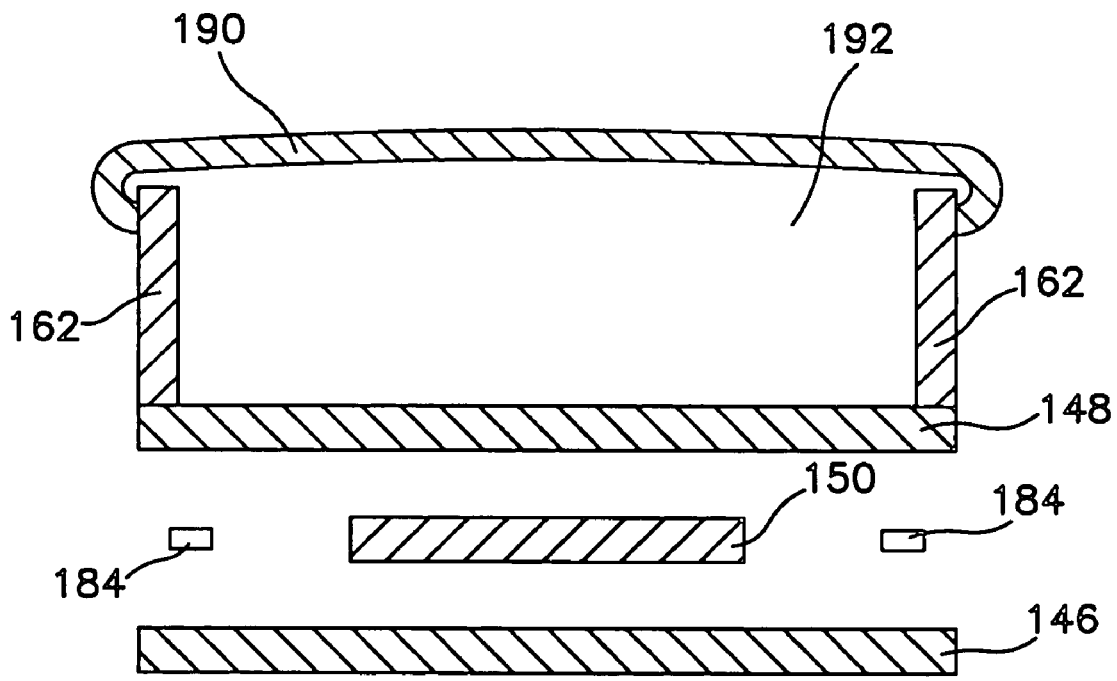
FIG. 11B is a cross-sectional view of FIG. 10 along line 11—11, showing the containment flaps in the perpendicular position.
Figure 12:
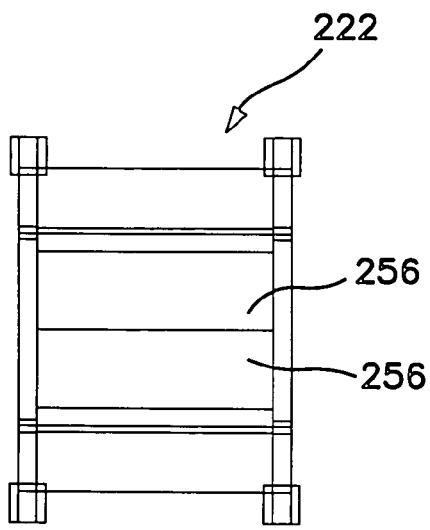
FIG. 12 is a top view of a water tank.
Figure 13:
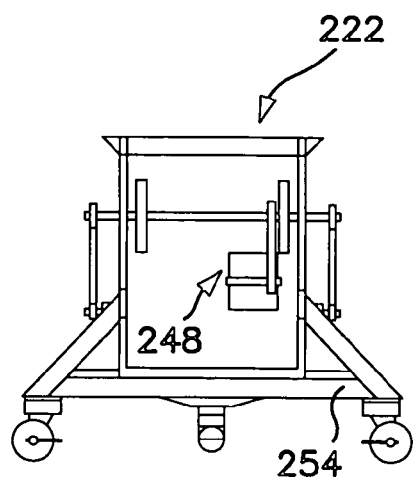
FIG. 13 is a side view of the water tank of FIG. 12.
Figure 14:
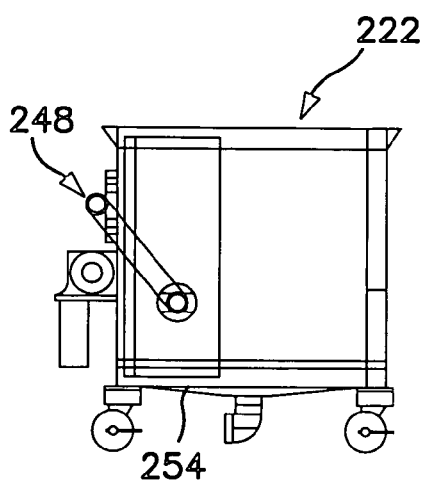
FIG. 14 is a front view of the water tank of FIGS. 12 and 13.
Figure 15:
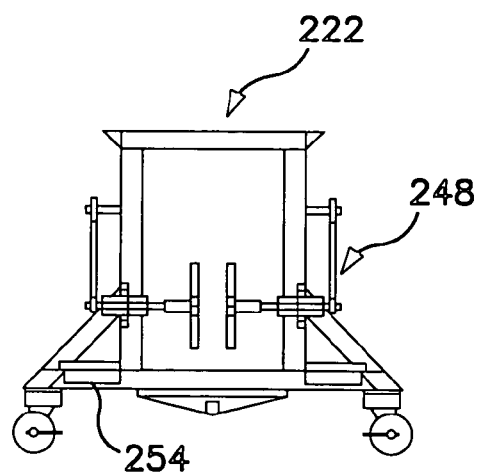
FIG. 15 is a side view of the water tank of FIGS. 12–14, opposite the side shown in FIG. 13.

The attachment of the mesh liner 190 on top of the containment flaps 162 leaves an unattached space 192 between the mesh liner 190 and the body side liner 148, as shown in FIG. 11B. If bowel movement particulate or liquid material does pass through the mesh liner 190 into the unattached space 192, the containment flaps 162 act as another barrier to the bowel movement material slipping out of the swimpant 120 completely.

The absorbent assembly 150 is intended to absorb urine, but does not swell excessively in the presence of swim water, such as pool or lake water. Furthermore, the absorbent assembly 150 is also intended to maintain a low hydrostatic pressure against the liquid-permeable outer cover due to urine insults prior to swimming. This can be achieved through the use of surge materials, superabsorbent materials, stabilized airlaid absorbent structures, coform, and the like. The composition of the absorbent assembly 150 is explained in greater detail below. In general, the materials of the absorbent assembly 150 can be configured in various ways to achieve fast intake and to generate void volume in order to prevent excess fluid from reaching the outer cover, the containment flaps, or any other barrier materials. The materials of the absorbent assembly 150 can also be configured to direct incoming fluid parallel to the longitudinal centerline 186 (FIG. 6B) of the swimpant 120, and inhibit fluid movement away from the centerline 186 toward the containment flaps, as is known in the art.

When the swimpant 120 is submerged in water for a length of time, such as when a wearer is swimming or wading in a pool or a lake, the swimpant 120 may fill with water. Solid bowel movement material is kept inside the swimpant 120 regardless of any release of swim water, because the mesh liner 190 and other pant components are constructed as in a normal absorbent garment, such as a diaper or training pant, to keep bowel movements contained.

The absorbent assembly 150, positioned between the outer cover 146 and the body side liner 148, can be any structure which is generally compressible, conformable, non-irritating to the child's skin, and capable of absorbing and retaining liquids and certain body wastes. The absorbent assembly 150 can be manufactured in a wide variety of sizes and shapes, and from a wide variety of liquid absorbent materials commonly used in the art. For example, the absorbent assembly 150 can suitably include a matrix of hydrophilic fibers, such as a web of cellulosic fluff, and the cellulosic fluff can be mixed with particles of a high-absorbency material commonly known as superabsorbent material. In a particular embodiment, the absorbent assembly 150 includes a matrix of cellulosic fluff, such as wood pulp fluff, and synthetic fibers. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be non-uniformly mixed. The fluff and superabsorbent particles can also be selectively placed into desired zones of the absorbent assembly 150 to better contain and absorb body exudates. The concentration of the superabsorbent particles can also vary through the thickness of the absorbent assembly 150. Alternatively, the absorbent assembly 150 can include a laminate of fibrous webs and superabsorbent material or other suitable means of maintaining a superabsorbent material in a localized area. Another type of absorbent material suitable for the absorbent assembly 150 is coform, which is a blend of short fibers and melt-blown fibers. The weight ratio of short fibers to melt-blown fibers may range between 30 (short)/70 (melt-blown) and 90 (short)/10 (melt-blown). Wood pulp fibers are preferred for the short fibers and polypropylene is preferred for the melt-blown fibers. Other short fibers such as short cut polypropylene, polyester, nylon, and the like can be substituted for part of or all of the wood pulp fibers. Superabsorbent materials can be added to the coform to increase capacity.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 150 is generally rectangular in shape, and includes a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent assembly 150 in an amount of from about 0 to about 90 weight percent based on total weight of the absorbent assembly 150. The absorbent assembly 150 suitably has a density within the range of about 0.10 to about 0.35 grams per cubic centimeter. The absorbent assembly 150 can be wrapped or encompassed by a suitable tissue wrap that maintains the integrity and/or shape of the absorbent assembly 150.

The outer cover 146 suitably includes a material that is substantially liquid-impermeable. The outer cover material 146 can be elastic, stretchable or nonstretchable. The outer cover 146 can be a single layer of material or a multi-layered laminate structure. For instance, the outer cover 146 can include a liquid permeable outer layer 170 and a liquid-impermeable inner layer 172 (FIGS. 7 and 9) that are suitably joined together by a laminate adhesive (not shown) or by thermal bonding. Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A.

The liquid-permeable outer layer 170 can be any suitable material and desirably one that provides a generally cloth-like texture. One example of such a material is a 20 gsm (grams per square meter) spunbond polypropylene non-woven web. The outer and inner layers 170 and 172 can also be made of those materials of which liquid permeable body side liner 148 is made. Other examples include polyolefin or other thermoplastic nonwoven webs having basis weights of about 1–100 gsm, including spunbond webs, meltblown webs, bonded carded webs, airlaid webs, and combinations of the foregoing, such as spunbond/meltblown webs and spunbond/meltblown/spunbond webs.

The inner layer 172 of the outer cover 146 is desirably manufactured from a thin plastic film, although other flexible liquid-impermeable materials can also be used. If the outer cover 146 is a single layer of material, it can be embossed and/or matte finished to provide a more cloth-like appearance.

The liquid-impermeable material can permit vapors to escape from the interior of the disposable absorbent article, while still preventing liquids from passing through the outer cover 146. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn. Other similar materials with varying degrees of liquid permeability are spunbond meltblown webs, spunbond/meltblown/spunbond hydrophobic, uniformly formed spunbond, or bi-component webs. A balance of barrier and permeability can be adjusted with fiber size and basis weight.

The liquid-permeable body side liner 148 is illustrated as overlying the outer cover 146 and absorbent assembly 150 (FIGS. 6B, 8A and 8B), and can but need not have the same dimensions as the outer cover 146. The body side liner 148 is desirably compliant, soft feeling, and non-irritating to the child's skin. Further, the body side liner 148 can be less hydrophilic than the absorbent assembly 150, to present a relatively dry surface to the wearer.

The body side liner 148 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the body side liner 148. For example, the body side liner 148 can be composed of a meltblown or spunbonded web of polyolefin fibers. The body side liner 148 can also be a bonded-carded web composed of natural and/or synthetic fibers. The body side liner 148 can be composed of a substantially hydrophobic material, and the hydrophobic material can, optionally, be treated with a surfactant or otherwise processed to impart a desired level of wettability and hydrophilicity. For example, the material can be surface treated with about 0.28 weight percent of a surfactant commercially available from the Rohm and Haas Co. under the trade designation Triton X-102. Other suitable surfactants are commercially available from Uniqema in Wilmington, Del., under the trade designation Ahcovel, and from Henkel KGAA Corporation in Dusseldorf, Germany, under the trade designation Glucopon 220. The surfactant can be applied by any conventional means, such as spraying, printing, brush coating or the like. The surfactant can be applied to the entire body side liner 148 or can be selectively applied to particular sections of the body side liner 148, such as the medial section along the longitudinal centerline.

A suitable liquid permeable body side liner 148 is a nonwoven bicomponent web having a basis weight of about 27 gsm. The nonwoven bicomponent can be a spunbond bicomponent web, or a bonded carded bicomponent web. Alternatively, the body side liner 148 can be a 15–30 gsm homofil polypropylene spunbond or bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 146 and body side liner 148 can include elastomeric materials, it can be desirable in some embodiments for the composite structure to be generally inelastic, where the outer cover 146, the body side liner 148 and the absorbent assembly 150 include materials that are generally not elastomeric.

The containment flaps 162 can be made of those materials of which the outer cover 146 and/or the body side liner 148 is made.

As noted previously, the illustrated swimpant 120 can have front and back side panels 142 and 144 disposed on each side of the absorbent chassis 132 (FIGS. 6A, 6B, 8A, 8B and 10). These transversely opposed front side panels 142 and transversely opposed back side panels 144 can be permanently bonded to the composite structure 140 of the absorbent chassis 132 and can be permanently bonded to one another along corresponding sides. Alternatively, the front and back side panels 142, 144 can be releasably attached to one another by a fastening system 168. The side panels 142 and 144 can be attached to the composite structure 140 and/or to one another using attachment means known to those skilled in the art such as adhesive, thermal or ultrasonic bonding. The side panels 142 and 144 can also be formed as a portion of a component of the composite structure 140, such as the outer cover 146 or the body side liner 148.

Suitable elastic materials, as well as one described process of incorporating elastic side panels into an absorbent garment, are described in the following U.S. patents: U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material includes a stretch-thermal laminate (STL), a neck-bonded laminated (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material can include other woven or nonwoven materials, such as those described above as being suitable for the outer cover 146 or body side liner 148, or stretchable but inelastic materials.

To further enhance containment and/or absorption of body exudates, the swimpant 120 can include waist elastic members 182 and/or leg elastic members 184, as are known to those skilled in the art (FIGS. 6A, 6B, 8A, 8B and 10). The waist elastic members 182 can be operatively joined to the outer cover 146 and/or to the body side liner 148, and can extend over part or all of the waist edges 138, 139. The leg elastic members 184 are desirably operatively joined to the outer cover 146 and/or to the body side liner 148 longitudinally along the opposite side edges 136 and positioned in the crotch region 126 of the swimpant 120. Any of the previously described elastic materials can be suitable for the waist elastic members 182 and the leg elastic members 184.

As described herein, the various components of the swimpant 120 can be integrally assembled together employing various types of suitable attachment means, such as adhesive, sonic and thermal bonds or combinations thereof. The resulting product is a swimwear garment 120 that provides bowel movement containment while keeping sand away from a wearer's skin within the garment.

Test Methods

1. Test Method: Wet Tensile Strength

This procedure is a bench test to determine the breaking load of a wet material before rupture occurs.

1. Overview

Wet samples are prepared according to the "Wet Sample Preparation Method" set forth below. A pre-wet material sample is placed between clamps on a tensile tester; the width of the material to be tested is 4 inches (102 mm). The gage length is 3 inches (76 mm) between the ends of the clamp faces. The term "load" refers to the force value measured by the load cells in the tensile tester.

The material to be tested is cut to provide a uniform 4 inch (102 mm) sample width. Samples should be at least 6 inches (153 mm) in length.

The jaws are separated until the specimen breaks. The load values generated on the material throughout this process are recorded. If slippage of specimens between the jaws occurs during testing, the grip faces of the jaws can be adapted to increase friction with specimens.

2. Apparatus and Materials 2.1 Constant Rate of Extension (CRE) tensile tester: MTS tensile tester model Synergie 200 Test Bed; available from MTS® Systems Corporation, Research Triangle Park, N.C. USA.

2.2 Load cells: A suitable cell selected so the majority of the peak load values fall between the manufacturer's recommended ranges of load cell's full scale value such as a 100N load cell available from MTS® Systems Corporation, Research Triangle Park, N.C. USA.

2.3 Operating software and data acquisition system: MTS TestWorks® for Windows software version 4; available from MTS® Systems Corporation, Research Triangle Park, N.C. USA.

2.4 Grips: pneumatic-action grips, top and bottom, identified as part number 2712-003 available from Instron Corporation, Canton, Mass. USA.

2.5 Grip faces: 25 by 76-mm (1 by 3-inch).

3. Conditioning

Conduct test in standard ASTM laboratory conditions: atmosphere of 23±2° C. (73.4±3.6° F.) and 50±5% relative humidity. The products should be measured after they equilibrate to laboratory conditions.

4. Test Specimen

A material specimen that is at least 6 inches (153 mm) in length (the direction of tensile testing) and is 4 inches (102 mm) in width (perpendicular to testing) should be used.

At least three specimens of each sample should be tested, and the results averaged.

5. Procedure

| Tensile Tester test conditions: | |
| --- | --- |
| Break sensitivity | 20% drop from peak load |
| Break percent drop | 100% |
| Break threshold | 0.5 pounds of force |
| Data acquisition rate | 100 Hz |
| Extension limit | 30.0 inches |
| Hold time 1 | 0 sec |
| Hold time 2 | 0 sec |
| Load limit high | 112 lb |
| Slowdown extension | 0 mm |
| Test speed | 12.00 inches/min |
| Zero extension after preload | Yes |
| Full scale load | 10,000 g |
| Gage length: | 3 inches (76 mm) |
| Number of cycles: | 1 |

A. Calibrate the load cell using the Testworks software, at the beginning of each work session.

B. Using the tensile frame pushbutton controls for crosshead position, move grips to provide a gage length of 3 inches (76 mm). Calibrate the software to this initial gage length.

C. Zero the load cell before each sample, or whenever the load cell appears to be drifting; no specimen should be in the cell when it is zeroed.

D. Place a material specimen so that it is centered between the grips, held in a centered position within each grip, and oriented correctly (4 inch/102 mm dimension running the width direction on the grips, approximately 1.5 inch of material held in each grip).

E. Close the grips on the specimen, holding the specimen in such a way as to minimize slack in the specimen, but do not place the specimen under tension. Ensure that the load at this point is less than five grams. If the load is greater than five grams, release the lower grip. Reclose the lower grip, again ensuring that the specimen is neither under tension nor buckled with excessive slack. Continue checking the starting load and following the above procedure until the starting load is under five grams. If the load is not below five grams when the sample is suspended from only the top grip, return to step C and zero the load cell.

F. Run the single cycle test using the above parameters by clicking on the RUN button.

G. When the test is complete, save the data to a sample file.

H. Remove the specimen from the grips.

I. Run additional specimens of a given sample using steps D–F and H; the data for all specimens should be saved to a single file.

J. Continue testing all samples in this manner.

K. Report the average peak load for each sample.

Wet Sample Preparation Method

Wet product samples for tensile testing are prepared using a method in which each product is exposed to conditions consistent with wetting and wear in a swimming environment. Each product is mounted on a mannequin and the assembly is placed in a water tank, where it undergoes motions typical of swim activities. Following this pretreatment, the wet product is removed and the swim liner material is tested according to the Wet Tensile Strength test method outlined above.

An appropriately sized mannequin of a human form from waist to knee should be obtained for pretreating wet samples. The desired dimensions of a mannequin for a given size of wearer may be identified using anthropometric data, for example. The mannequin should be of a construction that is able to reproduce the desired swim motions within the water tank (described below).

An industrial design firm, such as Joel Wittkamp Design, Inc. of Morrisville, N.C., can produce a mannequin according to specifications. A skeletal system can be designed to provide maximum flexibility and durability, while at the same time being characteristic of human skeletal features. The design of the structure and selection of the materials can be made to simulate human biological characteristics, such as bone structure, muscle tone, and skin surface tension, if desired. The mannequin needs to possess sufficient flexibility to withstand the conditions of the simulated swim motions.

The skeletal structure of the mannequin can be made using formed polyurethane components. Hip joints can be simulated using eyebolts. Waterproof polymers can be used to simulate muscle and skin tissue and provide the flexibility and durability required for carrying out the pretreatment. One suitable polymer is a soft, stretchable polyurethane material available from BJB Enterprises, Inc. of Tustin, Calif., under the trade designation Skinflex III.

Figure 16:
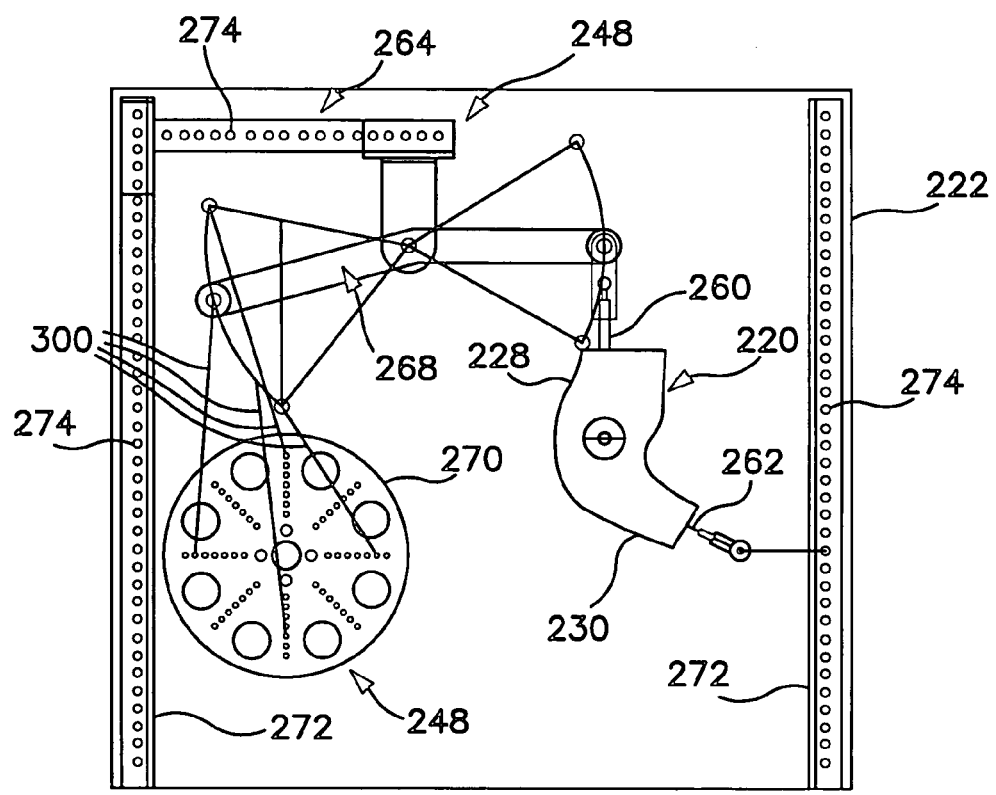
FIG. 16 is a side view of a water tank with a mannequin therein poised for simulated jumping.

The mannequin 220 is suitably attached to a motion mechanism 248 at the torso region 228 of the mannequin 220, as shown in FIG. 16. The motion mechanism 248 controls the movement of the mannequin 220. The motion mechanism 248 can be detached from the mannequin 220 in order to change the mannequin due to wear and tear, transport, or necessity to try a mannequin of a different size, mobility, or with different torso-leg angles. To attach the torso region 228 of the mannequin 220 to the motion mechanism 248, a rod 260 that is inserted into the mannequin 220 and protrudes roughly 3 inches above the torso region 228 can be connected to the motion mechanism 248.

The thigh or leg region 230 of the mannequin 220 is suitably attached to the side of the tank 222 by connection to a mounting bracket 272 and can be detached and rotated in order to put the stand-alone disposable pant liner 20 on relatively easily. To attach the thigh region 230 of the mannequin 220 to the tank 222, a rod 262 that is inserted into the mannequin 220 and protrudes roughly 2.5 inches beyond the thigh region 230 can be connected to the mounting bracket 272, as shown in FIG. 16.

Once the mannequin 220 is anchored to the motion mechanism 248 and to the tank 222, the torso portion 228 can be driven to create the desired swim movements. The motion mechanism 248, shown in FIG. 16, includes stainless steel mechanical components within the water tank 222, along with a variable speed motor (not shown) attached to the exterior of the tank, that can simulate the swim motions. Alternatively, an air cylinder can be used to simulate the swim motions.

Referring to FIG. 16, the motion mechanism 248 can include components such as a horizontal mounting bracket 264 attached to the tank 222, a pivot assembly 268 attached to the horizontal mounting bracket 264, and a drive wheel 270 mounted in/on the side walls of the tank 222 and driven by the variable speed motor (not shown). Motion mechanism 248 can also include hardware used to connect parts of the motion mechanism 248 to other parts of the mechanism 248, and to connect the mannequin 220 to various points of the motion mechanism 248 in order to simulate the swim motions.

The drive wheel 270 can be reamed or drilled at various points to provide attachment points for connecting bars and other hardware, and to adapt the wheel for use with different sized mannequins. The wheel 270 can be mounted to a drive shaft for the motor. The wheel 270 can be mounted from one side only to permit connecting bars to rotate freely across the face of the wheel when connected on the other side of the wheel. Attachment of pivot assembly 268 of the mannequin 220 to drive wheel 270, either directly or via connecting rods, can be used to drive the mannequin 220 to simulate the swim motions.

The wheel 270 can have holes provided at various increments from the center of the wheel to facilitate attachment of connecting rods for linkage to mannequin 220 or other hardware. The range of increments can provide a sensitive adjustment for the scale of motions simulated by the motion mechanism and mannequin. A connecting rod can be attached to the wheel in any manner so as to provide free rotation of the connecting rod end around a fixed attachment point on the wheel as the wheel rotates.

The horizontal mounting bracket 264 can be attached to attachment points 274 along vertical mounting brackets 272 of the tank 222 in a horizontal orientation at an elevation permitting the mannequin 220 to be suspended above the floor of the tank. The horizontal mounting bracket 264 can provide attachment points 274 along the bracket, at which points the motion mechanism 248 may be attached.

The pivot assembly 268 can comprise attachment points at center and end portions, and be attached to the horizontal mounting bracket 264 at the center point of the pivot, as shown in FIG. 16. Attachment points of the pivot assembly can be designed to allow the connected hardware to pivot freely in the plane of the assembly during motion of the pivot assembly. The beam can be angled to an extent dictated by the scale of other hardware in the system, in order to maintain the mannequin 220 submerged but above the base of the tank 222 during all motions of the beam. The pivot assembly 268 can further be attached at one end to the torso 228 of the mannequin 220, and be attached at the other end to the drive wheel 270, as illustrated in FIG. 16.

The swim motions can be simulated using specific connections between the drive wheel 270 and the mannequin, as well as a specific rate of rotation of drive wheel 270, as is described herein. The lengths and positioning of connecting rods and relative positions of mannequin, pivot assembly, horizontal mounting bracket, and drive wheel can be selected to provide the desired positions and ranges of motions during rotations of the drive wheel. These selections may be adapted as required for different sized mannequins, or any other necessary adjustments. The mechanisms used to join rods to hardware and to mannequin 220, and to join mannequin 220 to hardware, should be selected to provide the required mobility at each respective joint.

The water tank 222 used to carry out the invention should be large enough to hold enough water to cover the mannequin 220 as the mannequin performs the desired motions A suitable size for a water tank 222 used for testing child-sized mannequins is approximately 3 feet by 4 feet by 4.5 feet. The tank 222 can have vertical mounting brackets 272 centered on the walls in front and behind the mannequin, onto which the mannequin 220 and/or parts of the motion mechanism 248 can be mounted.

An up and down plunging motion can provide a jumping motion. The mechanical plunging motion can be achieved by attaching the upper torso of the mannequin 220 to an end of a pivot assembly 268 that is attached to the top assembly bracket of the water tank by a center, or pivot, point. The opposite end of the pivot assembly 268 can be attached to the drive wheel 270. When the pivot assembly 268 has partially or fully raised the mannequin, the legs of the mannequin can be attached to the side wall with connecting bars to provide a desired amount of bend in the mannequin's leg on the down stroke of the motion. More specifically, the jumping motion can be performed using the water tank set-up described and, as illustrated in FIG. 16.

The water tank 222, shown in detail in FIGS. 12–15, can be clear on all sides, including the bottom, for easy viewing. Furthermore, the water tank 222 can be supported on a stand 254 that holds the tank around chest height for easy viewing. The tank 222 may be portable and can have a splashguard 256 on top that opens like a door for easy access. The water tank 222 can hold approximately 175 gallons of water, or can be tailored to any other suitable size.

To set up the apparatus, one end of a connecting rod 300 can be connected to the drive wheel 270 by placing a pin through a ball joint end of the rod into a hole in the drive wheel 270, as shown in FIG. 16. The opposite end of the connecting rod 300 can be attached to the pivot assembly 268 (FIG. 16), and the horizontal mounting bracket 264 can be attached to the vertical mounting bracket 272 on the same side of the tank 222 as the drive wheel 270, at the top of the tank. The center point of the pivot assembly 268 can be attached to the horizontal bracket 264 at the top of the water tank 222. The mannequin 220 can be attached to the free end of the pivot in the manner shown in FIG. 16. The joining of the mannequin 220 to the free end of the pivot assembly 268 should be such that the torso of the mannequin 220 can move in relation to the free end, in the plane of the assembly. Finally, the legs of the mannequin can be flexibly connected to the opposite side wall of the tank along vertical mounting bracket 272. The rods used to connect the legs to the vertical mounting bracket 272 can be selected and positioned to provide the desired amounts of bend (see stepwise procedure below) in the mannequin's 220 body at the extreme positions of the plunging motion.

A plunging motion can then be carried out by driving the torso 228 up and down using the motor and attachments described above. The motion can be carried out at a speed of one cycle of the drive wheel per second, for an overall time of five minutes.

Using an electric digital flowmeter, approximately 175 gallons of water can be added to the water tank. Tap water is sufficient. An example of a suitable flowmeter is Model A104GMN100NA1*0, available from Great Plains Industries, Inc., of Wichita, Kans. A thermometer can be positioned inside the tank for monitoring water temperature.

1. Fill the water tank with 175 gallons of 78–82° F. water, as follows:
   A. Slowly turn water on until LED on flowmeter is readable.
   B. Reset the flowmeter to zero by holding down the "Display" button until display resets to zero.
   C. Open both hot and cold water valves to allow for maximum water flow.
   D. Monitor water temperature to ensure 78–82° F. water.
   E. When flowmeter reads 175 gallons, turn water off.
   F. Immediately detach water hose from water tank. If this is not done, the water will siphon out of the tank.
2. Apply first test product on mannequin prior to attaching mannequin to the water tank's motion components. Product should be pulled up tight in the crotch. If containment flaps are present in product make sure they are properly tucked inside product. Attach mannequin to motion components, as specified in motion instructions. Note: Attach mannequin to tank hardware after water tank is full. Water provides buoyancy, which helps to displace the weight of the mannequin.
3. When the mannequin wearing the product is in place in the tank, move the mannequin's legs through a cycle from an angle of about 85 degrees away from the body to an angle of about 135 degrees from the body. The frequency of motion is one cycle per second. This movement should continue for 5 minutes.
4. After the mannequin has performed this activity, the product is removed from the mannequin. The wet product is then used for tensile testing as described in the Wet Tensile Strength test method.

The samples used were the following:
1. 0.5 osy (ounces per square yard) polypropylene spunbond cloth, such as currently used in Huggies® Little Swimmers® Disposable Swimpants, not apertured
2. 0.6 osy polypropylene spunbond cloth, manufactured by Kimberly-Clark Corporation, Neenah, Wis., U.S.A., and apertured with a pin diameter size of 0.081 inches.
3. 0.9 osy polypropylene spunbond cloth, manufactured by Kimberly-Clark Corporation, Neenah, Wis., U.S.A., and apertured with a pin diameter size of 0.081 inches.
4. 1.2 osy polypropylene spunbond cloth, manufactured by Kimberly-Clark Corporation, Neenah, Wis., U.S.A., and apertured with a pin diameter size of 0.081 inches.

Wet Tensile Strength Data

| Sample | Wet Tensile Strength (in pounds of force) |
| --- | --- |
| 1 | 16.9 |
| 2 | 10.6 |
| 3 | 13.6 |
| 4 | 19.1 |

2. Test Method: Hole Size

Hardware:
1. Quantimet 970 or equivalent system; the Quantimet is currently available from Leica Microsystems AG of Wetzlar, Germany, E.U. This includes a No. 2 Chalnicon camera. The system employed for this testing uses RT11 operating system and a DEC-11 computer.
2. DCI HM1212 Autostage, 6 inches high, available from Industrial Devices Corp. of Novato, Calif., U.S.A.
3. Kreonite Mobile Studio Macroviewer, distributed by J. Kelly, Darien, Ill., U.S.A.
4. Collimating light box, made to dimensions of 10"H×12"W×12"D
5. 50 mm EL-Nikkor enlarging lens, used at f/2.8, manufactured by Nikon Corporation, Melville, N.Y., U.S.A.
6. 20 or 40 mm extension tube
7. 2 adaptors to convert lens fittings; one to convert EL to F type, one to convert F type to C type
8. Variable neutral density filter The samples used were the following:
1. Wire screen (such as is used in a sieve)
2. A bicomponent spunbond material with apertures
3. Grey textile lace; this material has apertures that have a crossbar spanning them (crossbar is part of the fabric). The material was examined as-is. This material was purchased at Hancock Fabrics in Appleton, Wis., U.S.A.
4. Repeat of sample #3, but the crossbars were removed to leave larger apertures.
5. 0.5 osy (ounces per square yard) polypropylene spunbond material such as currently used in Huggies® Little Swimmers® Disposable Swimpants, not apertured.

| Sample | 1 | 2 | 3 | 4 | 5 |
|---|---|---|---|---|---|
| Scanner IV | 4.09 | 0.00 | 0.00 | 0.00 | 4.06 |
| Scanner SENS | 2.54 | 2.58 | 2.58 | 2.58 | 2.07 |
| Cal Value | 12.21 microns | 20.22 microns | 20.22 microns | 20.22 microns | 9.135 microns |
| Amend stmt 1 | (OPEN by 2) | (CLOSE by 5) | (OPEN by 12) | (CLOSE by 3) | (OPEN by 1) |
| Amend stmt 2 | N/A | (OPEN by 5) | (CLOSE by 5) | (OPEN by 12) | N/A |
| Live Frame Rectangle | X: 190 Y: 170 W: 457 H: 408 | X: 190 Y: 170 W: 457 H: 408 | X: 190 Y: 170 W: 457 H: 408 | X: 241 Y: 206 W: 372 H: 471 | X: 127 Y: 99 W: 640 H: 570 |

For samples 2–5, a specimen of material was laid down onto the glass surface of the top of the collimating light box. For sample 1, a specimen was laid down onto the masked surface of the autostage. A piece of glass was then placed atop the specimen. The specimen was analyzed using fluorescent transmitted light, the camera, and the software routine identified below. Each experiment analyzed twelve fields of view on the specimen and grouped the hole size results from each. Hole sizes below 100 microns were excluded. At least three separate specimens of each sample were examined.

A mean hole size was determined by the software for each sample, as well as a standard deviation. The hole sizes are in microns and are based on ECD, Equivalent Circular Diameter.

Hole Size Data

| Sample | # specimens | mean, microns | st dev, microns |
|---|---|---|---|
| 1 | 4 | 147.3 | 0.5 |
| 2 | 3 | 884 | 39 |
| 3 | 3 | 3669 | 123 |
| 4 | 3 | 5810 | 54 |
| 5 | 3 | 81.5 | 1.63 |

Specific software settings were varied sample-to-sample. These variations were incorporated into the following overall software routine.

```
NAME=    LINER2
PURPOSE=    Measure % open and ECD of cover mat'l
Scanner    (No. 2 Chalnicon    LV = 0.00 SENS = 2.58)
SUBRTN STANDARD
Load Shading Corrector (pattern – LINRNS)
Calibrate User Specified (Cal Value = 20.22 microns per pixel)
FLAG3     :=    3.
STAGEX    :=    60000.
STAGEY    :=    140000.
Stage Move (STAGEX, STAGEY)
Pause Message
Please Position Sample
Pause
TOTFIELDS        :=    0.
Enter specimen identity
Scanner (No. 2 Chalnicon AUTO-SENSITIVITY LV = 4.24)
For SAMPLE = 1 to 1
Stage Scan (        X        Y
Scan origin    STAGEX    STAGEY
Field size     10000.0    10000.0
No of fields    3        4 )
For FIELD
Live Frame is Rectangle (X: 190, Y: 170, W: 457, H: 408, )
Detect 2D (Lighter than 52, Delin)
Amend    (OPEN by 12)
Amend    (CLOSE by 5)
Measure field – Parameters into array FIELD
PCTAREA    :=    FIELD AREAFRACT * 100.
Distribute COUNT vs PCTAREA (Units %      )
Into GRAPH from 0.00 to      60.00 into 15 bins, differential
TOTFIELDS := TOTFIELDS + 1.
Measure feature    AREA     X.FCP    Y.FCP
Into array FEATURE (of 1000 features and 5 parameters)
FEATURE CALC    :=    ( ( 4. * AREA/PI) ^ 0.50000 )
Distribution of COUNT v CALC (Units MICRONS)
From FEATURE in HIST01 from 50.00 to 10000.
In 25 bins (LOG)
Stage Step
Next FIELD
Pause
Next
Print " "
Print Distribution ( GRAPH, differential, bar chart, scale = 0.00 )
Print "COUNT VS PERCENT OPEN AREA"
Print " "
Print " "
Print Distribution ( HIST01, differential, bar chart, scale = 0.00)
Print "COUNT VS ECD HISTO"
Print " "
Print "Number of fields :" , TOTFIELDS
END OF PROGRAM
```

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A stand-alone disposable garment having a waist opening and two leg openings, comprising:
    a liquid-permeable nonwoven material that is also permeable to sand,
    a first side seam extending from the waist opening to a first leg opening; and
    a second side seam extending from the waist opening to a second leg opening;
    the garment being substantially free of an absorbent assembly and substantially free of liquid-impermeable material, wherein the garment is worn beneath swimwear and is not directly attached to the swimwear.

2. The stand-alone disposable garment of claim 1, wherein the liquid-permeable nonwoven material is a mesh material.

3. The stand-alone disposable garment of claim 1, wherein the nonwoven material comprises spunbond polypropylene.

4. The stand-alone disposable garment of claim 1, wherein the nonwoven material comprises spunbond polyethylene.

5. The stand-alone disposable garment of claim 1, wherein the nonwoven material comprises a spunbond/meltblown/spunbond web combination.

6. The stand-alone disposable garment of claim 1, wherein the liquid-permeable material comprises nylon.

7. The stand-alone disposable garment of claim 1 comprising at least two layers of the liquid-permeable material.

8. The stand-alone disposable garment of claim 1, wherein the material has a basis weight in a range from about 7 gsm to about 85 gsm.

9. The stand-alone disposable garment of claim 2, wherein the mesh material has a basis weight in a range from about 14 gsm to about 54 gsm.

10. The stand-alone disposable garment of claim 2, wherein the mesh material has a basis weight in a range from about 20 gsm to about 41 gsm.

11. The stand-alone disposable garment of claim 2, wherein the mesh material has a hole size in a range from about 147 microns to about 5810 microns.

12. The stand-alone disposable garment of claim 2, wherein the mesh material has a tensile strength of at least about 5 pounds of force per 4 inches of material.

13. The stand-alone disposable garment of claim 2, wherein the mesh material has a tensile strength of at least about 10 pounds of force per 4 inches of material.

14. The stand-alone disposable garment of claim 2, wherein the mesh material has a tensile strength of at least about 13 pounds of force per 4 inches of material.

15. The stand-alone disposable garment of claim 2, wherein the mesh material has a tensile strength of at least about 19 pounds of force per 4 inches of material.

16. The stand-alone disposable garment of claim 1 further comprising a waist elastic.

17. The stand-alone disposable garment of claim 1 further comprising a pair of leg elastics.

18. The stand-alone disposable garment of claim 17, wherein the leg elastics comprise curved elastics.

19. The stand-alone disposable garment of claim 17, wherein the leg elastics comprise straight elastics.

20. The stand-alone disposable garment of claim 1 wherein the first and second side seams each comprise a refastenable fastening system extending from the waist opening to each of the first and second leg openings, respectively.

21. The stand-alone disposable garment of claim 1 wherein each of the first and second side seams is permanently bonded.

22. The stand-alone disposable garment of claim 1, wherein the garment is a single-layer garment.

23. The stand-alone disposable garment of claim 1, wherein the garment is not worn in the absence of a separate swimwear garment.

* * * * *